(12) United States Patent
Gonsalves et al.

(10) Patent No.: US 7,833,690 B2
(45) Date of Patent: Nov. 16, 2010

(54) PHOTOACID GENERATORS AND LITHOGRAPHIC RESISTS COMPRISING THE SAME

(75) Inventors: Kenneth E. Gonsalves, Concord, NC (US); Mingxing Wang, Charlotte, NC (US)

(73) Assignee: The University of North Carolina at Charlotte, Charlotte, NC (US)

(*) Notice: Subject to any disclaimer, the term of this patent is extended or adjusted under 35 U.S.C. 154(b) by 382 days.

(21) Appl. No.: 11/544,463

(22) Filed: Oct. 6, 2006

(65) Prior Publication Data

US 2007/0117043 A1    May 24, 2007

Related U.S. Application Data

(63) Continuation-in-part of application No. 11/226,912, filed on Sep. 14, 2005, which is a continuation-in-part of application No. 09/992,560, filed on Nov. 5, 2001, now Pat. No. 7,008,749, and a continuation-in-part of application No. 10/324,642, filed on Dec. 19, 2002, now Pat. No. 7,049,044.

(60) Provisional application No. 60/763,738, filed on Feb. 1, 2006, provisional application No. 60/769,990, filed on Apr. 7, 2006.

(51) Int. Cl.
*G03C 1/73* (2006.01)
*G03F 7/004* (2006.01)
*G03F 7/029* (2006.01)

(52) U.S. Cl. .............. 430/270.1; 430/921; 430/925; 430/919; 568/28; 568/30; 568/31; 568/32; 568/33; 568/34; 568/35; 568/74; 568/75; 568/77; 522/31; 526/243; 526/245; 526/247; 526/248; 526/287; 526/288

(58) Field of Classification Search .............. None
See application file for complete search history.

(56) References Cited

U.S. PATENT DOCUMENTS 5,945,250 A * 8/1999 Aoai et al. .............. 430/270.1

| | | | |
|---|---|---|---|
| 6,869,748 B2 * | 3/2005 | Takeda et al. | 430/270.1 |
| 2002/0051928 A1 * | 5/2002 | Zampini | 430/138 |
| 2004/0029037 A1 * | 2/2004 | Kamabuchi et al. | 430/270.1 |
| 2004/0229161 A1 * | 11/2004 | Yasunami et al. | 430/270.1 |
| 2005/0208419 A1 * | 9/2005 | Inabe et al. | 430/270.1 |
| 2006/0121390 A1 * | 6/2006 | Gonsalves | 430/270.1 |

FOREIGN PATENT DOCUMENTS

| JP | 10-221852 | * | 8/1998 |
| JP | 11-167199 | * | 6/1999 |
| JP | 2003-322972 | * | 11/2003 |
| JP | 2006-178317 | * | 7/2006 |

OTHER PUBLICATIONS

English abstract for JP 10-221852 provided by JPO.*
Machine-assisted English translation for JP 10-221852 provided by JPO.*
Wang et al ("Novel Anionic Photoacid Generators (PAGs) and Corresponding PAG Bound Polymers", Macromolecular Rapid Communications, 2006, vol. 27, issue 18 (date Sep. 22, 2006).*
Machine-assisted English translation of JP2006-178317 provided by JPO.*
English abstract of JP2003-322972 provided by JPO.*
English abstract of JP11-167199 provided by JPO.*

* cited by examiner

*Primary Examiner*—Sin J. Lee
(74) *Attorney, Agent, or Firm*—J. Clinton Wimbish; Kilpatrick Stockton LLP

(57) ABSTRACT

The present invention relates to photoacid generating compounds, lithographic resists comprising photoacid generating compounds, and to various lithographic processes techniques, and applications. In one embodiment, the present invention provides a photoacid generator of Formula (I):

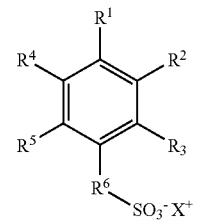

44 Claims, 26 Drawing Sheets

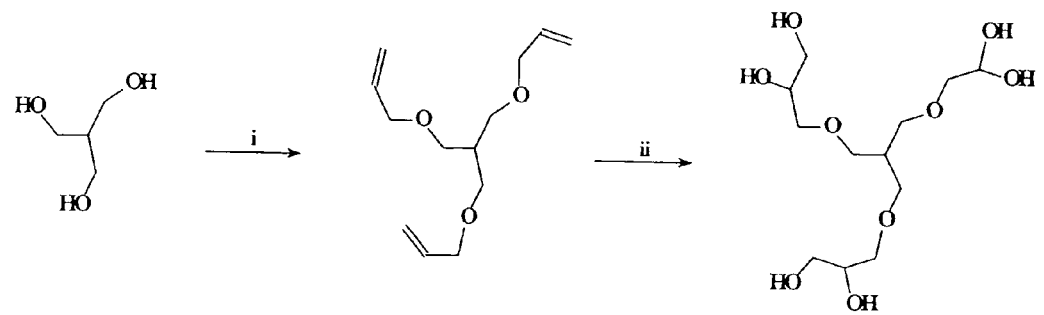

i. Bu$_4$NBr, NaOH, allyl chloride, toluene/water, 24h, 50 °C;

ii. OsO$_4$ (cat.), NMO, acetone/water/ter-butanol, 20h, 25 °C.

iii. Dry DMF, K$_2$CO$_3$, N$_2$, 80 °C.
    f: Cationic PAG or Anionic PAG
    g: t-Butyl or Adamantyl or THP groups
    h: 1. t-Butyl or Adamantyl or THP groups
       2. Cationic PAG or Anionic PAG f  g  h

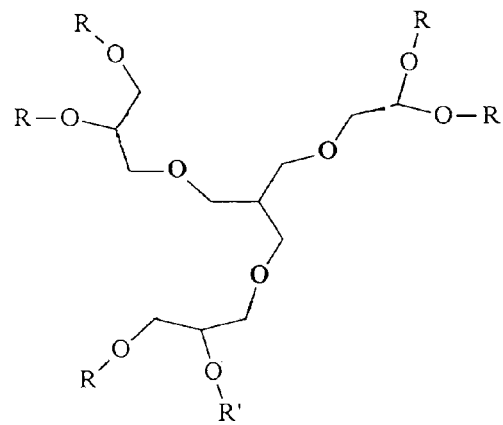

f £° R, R' = Cationic or Anionic PAG
g£° R, R' = t-butyl or adamantyl or THP groups
h£° R  = t-butyl or adamantyl or THP groups
     R' = Cationic or Anionic PAG

FIGURE 14

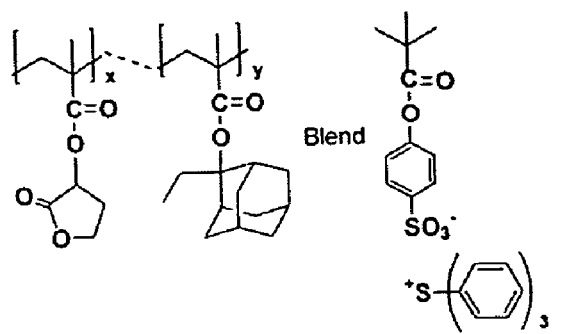
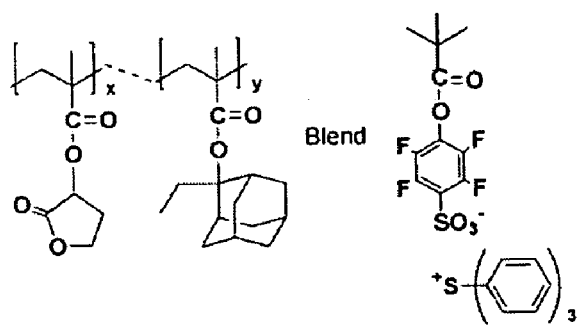
FIGURE 20

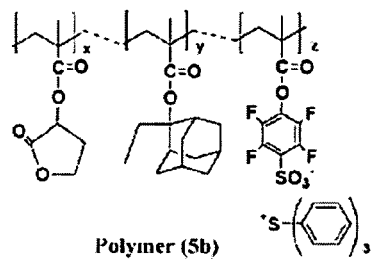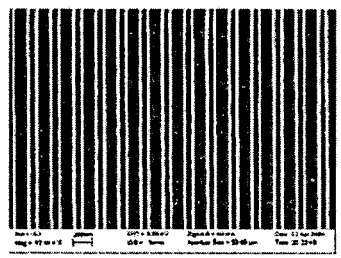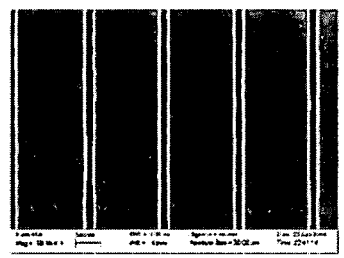
110 nm (11.5 mJ/cm$^2$)   80 nm (3.0 mJ/cm$^2$)
FIGURE 26

PHOTOACID GENERATORS AND LITHOGRAPHIC RESISTS COMPRISING THE SAME

PRIOR RELATED U.S. APPLICATION DATA

This application is a continuation in part of pending U.S. patent application Ser. No. 11/226,912 filed Sep. 14, 2005, which is a continuation in part of U.S. patent application Ser. No. 09/992,560 filed Nov. 5, 2001, now U.S. Pat. No. 7,008,749, and a continuation in part of U.S. patent application Ser. No. 10/324,642 filed Dec. 19, 2002, now U.S. Pat. No. 7,049,044. This application also claims priority to U.S. Provisional Patent Application Ser. No. 60/763,738 filed Feb. 1, 2006 and U.S. Provisional Patent Application Ser. No. 60/769,990 filed Apr. 7, 2006.

FIELD OF THE INVENTION

The present invention relates to photoacid generating compounds, lithographic resists comprising photoacid generating compounds, and to various lithographic processes techniques, and applications.

BACKGROUND OF THE INVENTION

Lithographic techniques for photoresist patterning with resolutions down to the 22 nm node are essential for future device miniaturization. (See: The 2003 Edition of the ITRS: Lithography, 2005 International Technology Roadmap for Semiconductors: http://public.itrs.net/2003). Patterning at the nanometer scale can be achieved in various ways including optical, atomic force microscope, scanning probe, electron beam, nanoimprint, and extreme ultraviolet lithography (EUV lithography). In order to keep pace with the demand for rapid printing of smaller features, it is necessary to gradually reduce the wavelength of light used for imaging and to design imaging systems with larger numerical apertures.

EUV lithography, for example, uses short wavelength (13.4 nm) radiation to administer projection imaging or lithographic patterning. As a result of its short wavelength radiation, EUV lithography has evolved into a possible candidate for the production of future integrated circuits at the 45 or 22 nm mode. Much of the work to date, however, has focused on aspects of lithography tool development as opposed to resist performance.

Two primary types of resist polymers that have been investigated are chain-scission resists and chemically amplified (CA) resists. Upon irradiation of a chain-scission resist film, the molecular weights of the polymers in the exposed regions are decreased via chain scission reactions arising from the irradiation. As a result, solubility differentiation is achieved between the exposed and the unexposed regions. Chemically amplified resists achieve solubility differentiation based on an acid-catalyzed deprotection reaction which changes the polarity of the polymer in the exposed region. A typical CA resist formula consists of a matrix polymer and a photoacid generator (PAG). Upon irradiation with an electron beam or extreme UV radiation, the PAG generates a strong acid that catalyzes the deprotection reaction.

Several classes of PAGs have been used in CA resists. These PAGs, however, are almost exclusively used in their small molecule forms, and small molecule PAGs typically exhibit limited compatibility with the resist polymer matrix. As a result, problems such as phase separation, non-uniform acid distribution, and non-uniform acid migration occurring during temperature fluctuations (e.g. variation in baking processing) may arise. Such limitations frequently lead to an undesirable, premature and non-uniform deprotection reaction in the CA resist film.

Moreover, resists for EUV lithography and other lithographic techniques must possess reasonable photospeed while maintaining a low level of outgassing components. Lithographic resists must additionally demonstrate high sensitivity, high contrast and resolution, low absorption, high dry-etch resistance, good adhesion to substrates, and low line-edge roughness. Current resists for sub-100 nm patterning applications, including EUV lithography, display poor etch resistance, poor outgassing properties, and undesirable absorption coefficients. As a result, it would be desirable to provide PAGs and resists that exhibit improved properties for lithographic processes such as EUV, X-ray (XRL), 193 nm, electron beam (EBL), and ion beam (IBL) lightographies.

SUMMARY OF THE INVENTION

The present invention addresses several of the current limitations in lithographic techniques by providing photoacid generators and lithographic resists comprising photoacid generators which can achieve high sensitivity, high contrast, high resolution, and/or high dry etch resistance for pattern transfer to a substrate. Moreover, the present invention provides photoacid generators and resists that address compatibility problems which can lead to phase separation, non-uniform acid distribution, and non-uniform acid migration occurring during temperature fluctuations.

In one embodiment, the present invention provides a photoacid generator of Formula (I):

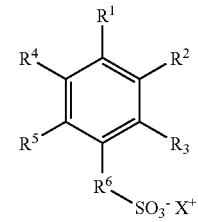

wherein $R^1$ is selected from the group consisting of -hydrogen, -alkyl, -alkenyl, -alkynyl, -cycloalkyl, -fluoroalkyl, -fluoroalkenyl, -fluoroalkynyl, -aryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, -carboxyl, and -hydroxyl; and wherein the alkenyl and the aryl groups of $R^1$ are optionally substituted 1 to 5 times with a substituent group, wherein the substituent group(s) are independently selected from the group consisting of -alkyl, -alkylene, -aryl, -carboxyl, and -hydroxyl.

$R^2$, $R^3$, $R^4$, and $R^5$ are independently selected from the group consisting of -hydrogen, -alkyl, -alkenyl, -fluoroalkyl, -fluoroalkenyl, —O-alkyl, -halo, -cyano, and -nitro.

$R^6$ is a direct bond or selected from the group consisting of alkyl or fluorinated alkyl.

$X^+$ is selected from the group consisting of a sulfonium compound and an ionium compound.

In another embodiment, the present invention provides a photoacid generator of Formula (II):

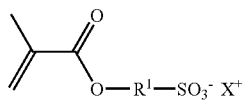

wherein $R^1$ is selected from the group consisting of alkylene, alkenylene, fluorinated alkylene, and fluorinated alkenylene; and $X^+$ is selected from the group consisting of a sulfonium compound and an ionium compound.

In another embodiment, the present invention provides a photoacid generator of Formula (III):

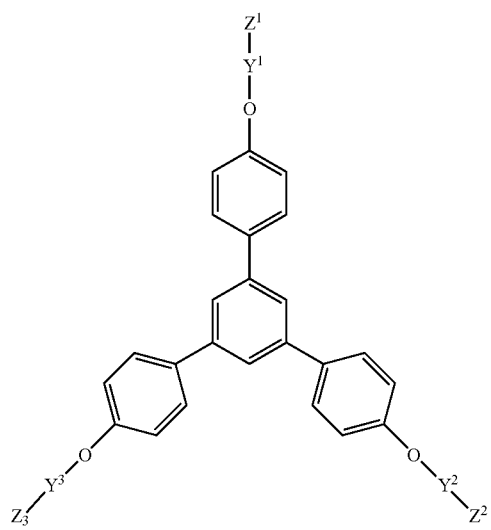

wherein $Y^1$, $Y^2$, and $Y^3$ are independently selected from the group consisting of alkylene, alkenylene, fluoroalkylene, and fluoroalkenylene.

$Z^1$, $Z^2$, and $Z^3$ are independently selected from the group consisting of:

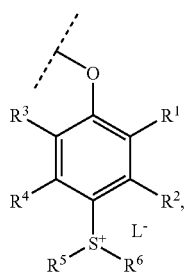 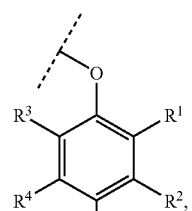

and —O—C(O)—O—$R^7$ wherein $R^1$, $R^2$, $R^3$, $R^4$, $R^5$, and $R^6$ are independently selected from the group consisting of -hydrogen, -alkyl, -alkylene, -fluoroalkyl, -fluoroalkenyl, -aryl, -substituted aryl, —O-alkyl, -halo, -cyano, and -nitro; and wherein $R^7$ is selected from the group consisting of -hydrogen, -alkyl, -alkenyl, -fluoroalkyl, -fluoroalkenyl, -pyranyl, and -adamantyl.

$L^-$ is selected from the group consisting of a sulfonate compound, $BF_4^-$, $PF_6^-$, and $SbF_6^-$; and $X^+$ is selected from the group consisting of a sulfonium compound and an ionium compound.

In a further embodiment, the present invention provides a dendrimer comprising at least one photoacid generator moiety. In some embodiments, a dendrimer comprises a plurality of photoacid generator moieties. In addition to at least one or a plurality of photoacid generating moieties, a dendrimer, in some embodiments, comprises at least one acid labile protecting group or a plurality of acid labile protecting groups. An acid labile protecting group, according to embodiments of the present invention, is operable to undergo acid catalyzed cleavage resulting in at least a partial polarity change of the molecule with which the acid labile protecting group was associated.

In one embodiment, the present invention provides a dendrimer comprising at least one acid labile protecting group and no photoacid generating moieties. In another embodiment, the present invention provides a dendrimer comprising a plurality of acid labile protecting groups and no photoacid generating moieties.

Dendrimers comprising photoacid generating moieties and/or acid labile protecting groups, according to some embodiments of the present invention, comprise zero generation (G0), first generation (G1), second generation (G2), third generation (G3), fourth generation (G4), fifth generation (G5), and greater than fifth generation (G5) dendrimers.

In some embodiments, the present invention provides a dendrimer of Formula (IV):

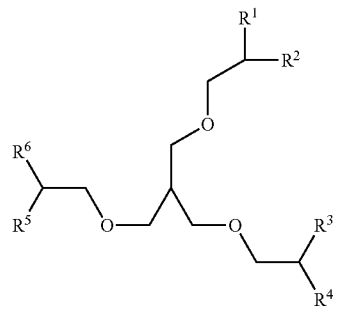

wherein $R^1$, $R^2$, $R^3$, $R^4$, $R^5$, and $R^6$ are independently selected from the group consisting of:

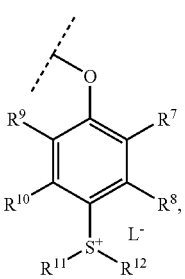 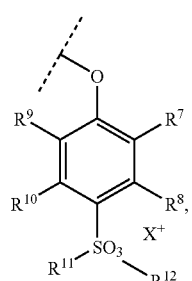

and —O—C(O)—O—$R^{13}$ wherein $R^7$, $R^8$, $R^9$, $R^{10}$, $R^{11}$, and $R^{12}$ are independently selected from the group consisting of -hydrogen, -alkyl, -alkylene, -fluoroalkyl, -fluoroalkenyl, -aryl, -substituted aryl, —O-alkyl, -halo, -cyano, and -nitro; and
wherein $R^{13}$ is selected from the group consisting of -hydrogen, -alkyl, -alkenyl, -fluoroalkyl, -fluoroalkenyl, -pyranyl, and -adamantyl.
$L^-$ is selected from the group consisting of a sulfonate compound, $BF_4^-$, $PF_6^-$, and $SbF_6^-$; and
$X^+$ is selected form the group consisting of a sulfonium compound and an ionium compound.

In another aspect, the present invention provides lithographic resists comprising photoacid generators and/or dendrimers as described herein. In one embodiment, the present invention provides a lithographic resist comprising at least one photoacid generator of Formula (I). In another embodiment, the present invention provides lithographic resist comprising at least one photoacid generator of Formula (II). In another embodiment, the present invention provides a lithographic resist comprising at least one photoacid generator of Formula (III). A lithographic resist, in some embodiments, comprises a plurality of photoacid generators of Formula (I), Formula (II), and/or Formula (III). In a further embodiment, the present invention provides a lithographic resist comprising at least one dendrimer of Formula (IV).

In one embodiment, the present invention provides a lithographic resist comprising an adamantyl component and a photoacid generating component, wherein the photoacid generating component comprises at least one photoacid generator of Formula (I), Formula (II), and/or Formula (III). In some embodiments, the photoacid generating group comprises a plurality of photoacid generators of Formula (I), Formula (II), and/or Formula (III).

A lithographic resist comprising an adamantyl component and a photoacid generating component, in some embodiments, further comprises a hydroxystyrene component or a γ-butyrolactone component. In some embodiments, the adamantyl component and hydroxystyrene component or γ-butyrolactone component are copolymerized.

In some embodiments, the photoacid generating component is blended with the adamantyl component. In other embodiments, the photoacid generating component is incorporated into the polymeric backbone of the polymeric resist through copolymerization with the adamantyl component.

In another embodiment, a lithographic resist comprises a photoacid generating component comprising a photoacid generator of Formula (III), wherein the lithographic resist does not comprise a polymeric component. In a further embodiment, a lithographic resist comprises a dendrimer comprising photoacid generating moieties and/or acid labile protecting groups, wherein the lithographic resist does not comprise a polymeric component. In one embodiment, a lithographic resist comprises a dendrimer of Formula (IV).

Polymeric resists of the present invention, in some embodiments, further comprise a base component. In one embodiment, the base component is blended in the polymeric resist. In another embodiment, the base component is part of the polymeric backbone of the polymeric resist.

Polymeric resists of the present invention, in some embodiments, further comprise a fullerene derivative. In one embodiment, the fullerene derivative is blended in the polymeric resist. In another embodiment, the fullerene derivative is part of the polymeric backbone of the polymeric resist.

In another aspect the present provides methods for producing lithographic resists. In one embodiment, a method of producing a resist comprises blending a photoacid generating component with a first component, wherein the photoacid generating component comprises at least one photoacid generator of Formula (I), Formula (II), and/or Formula (III). In some embodiments, the photoacid generating component comprises a plurality of photoacid generators of Formula (I), Formula (II), and/or Formula (III). In some embodiments, the first component comprises an adamantyl component. A method for producing a lithographic resist, in some embodiments, further comprises blending a photoacid generating component with a second component in addition to the first component. A second component, in some embodiments, comprises a hydroxystyrene component or a γ-butyrolactone component. In one embodiment, the first component and second component are copolymerized. Copolymerization of the first and second components, in some embodiments, is completed prior to blending the photoacid generating component.

A method for producing a lithographic resist, in another embodiment, comprises copolymerizing a first component and a photoacid generating component, wherein the photoacid generating component comprises at least one photoacid generator of Formula (I), Formula (II), and/or Formula (III). In some embodiments, the photoacid generating component comprises a plurality of photoacid generators of Formula (I), Formula (II), and/or Formula (III). The first component, in some embodiments, comprises a first monomer, first oligomer, and/or first polymer. In one embodiment, the first component comprises an adamantyl component.

In some embodiments, a method for producing a lithographic resist further comprises copolymerizing a second component with the first component and photoacid generating component. The second component, in some embodiments, comprises a second monomer, second oligomer, and/or second polymer. In one embodiment, the second component comprises a hydroxystyrene component or a γ-butyrolactone component.

In another aspect, the present invention provides lithographic processes. In one embodiment, a lithographic process of the present invention comprises exposing a lithographic recording medium to radiation to form a pattern, wherein the lithographic recording medium comprises a resist as described herein. In some embodiments, a lithographic process further comprises developing the pattern. In some embodiments of lithographic processes of the present invention, radiation used in the patterning of resists comprises extreme ultraviolet radiation (EUV), x-ray radiation, 193 nm radiation, electron beam radiation, ion beam radiation, or combinations thereof.

In a further aspect, the present invention provides integrated circuits prepared by lithographic processes utilizing the presently described resists.

These and other features, embodiments, objects, and advantages of the present invention will become apparent after a review of the following detailed description of the disclosed embodiments.

BRIEF DESCRIPTION OF THE FIGURES

FIG. 14 illustrates a reaction scheme for producing a dendrimer according to an embodiment of the present invention.

FIG. 20 illustrates a synthetic scheme for a polymeric resist according to an embodiment of the present invention.

FIG. 26 provides scanning electron microscope images of a polymeric resist according to an embodiment of the present invention.

DETAILED DESCRIPTION

Figure 1:
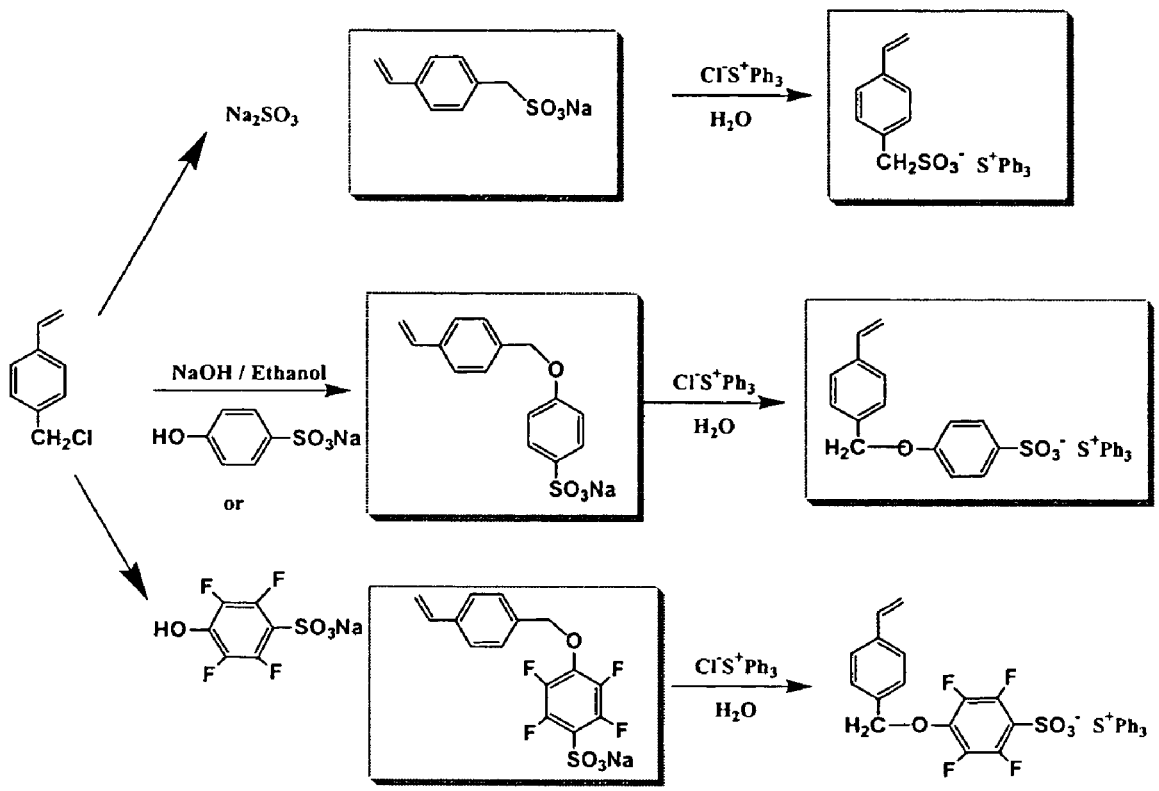
FIG. 1 illustrates a reaction scheme for producing photoacid generators according to an embodiment of the present invention.
Figure 2:
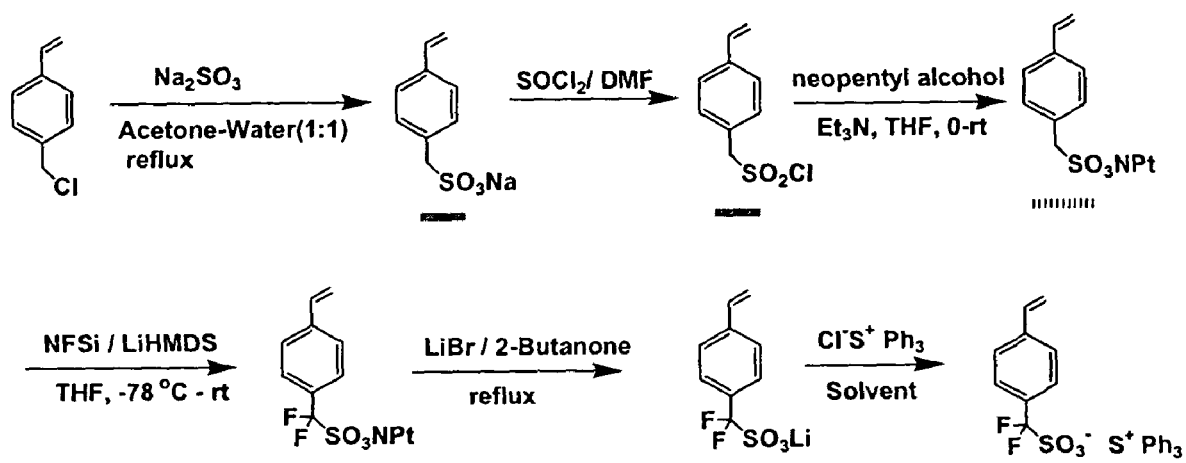
FIG. 2 illustrates a reaction scheme for producing a photoacid generator according to an embodiment of the present invention.
Figure 3:
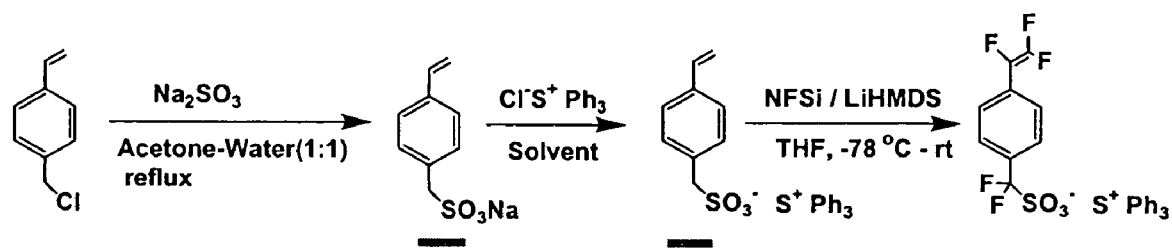
FIG. 3 illustrates a reaction scheme for producing a photoacid generator according to an embodiment of the present invention.
Figure 4:
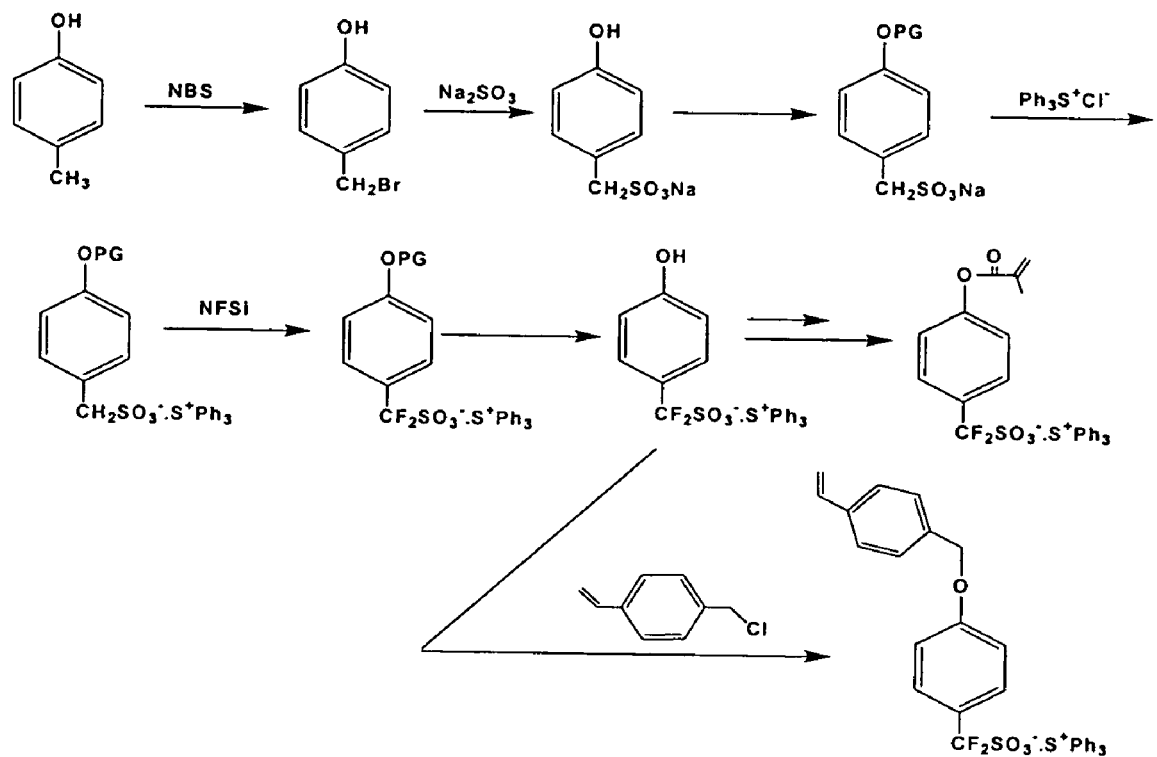
FIG. 4 illustrates a reaction scheme for producing a photoacid generator according to an embodiment of the present invention.
Figure 5:
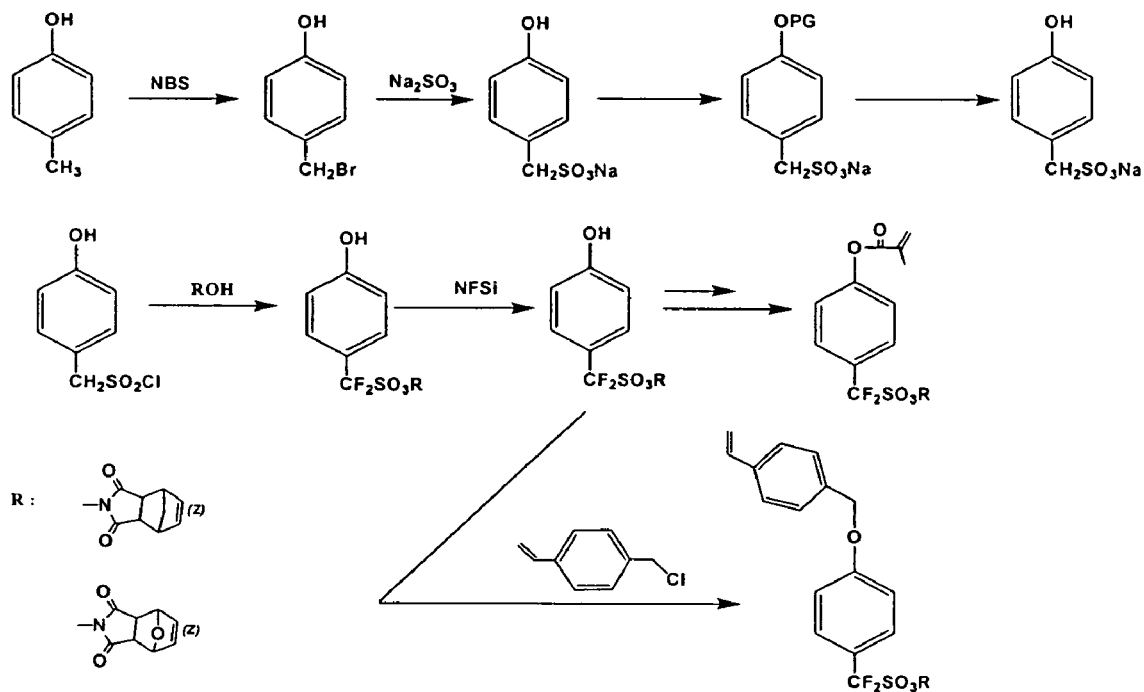
FIG. 5 illustrates a reaction scheme for producing a photoacid generator according to an embodiment of the present invention.
Figure 6:
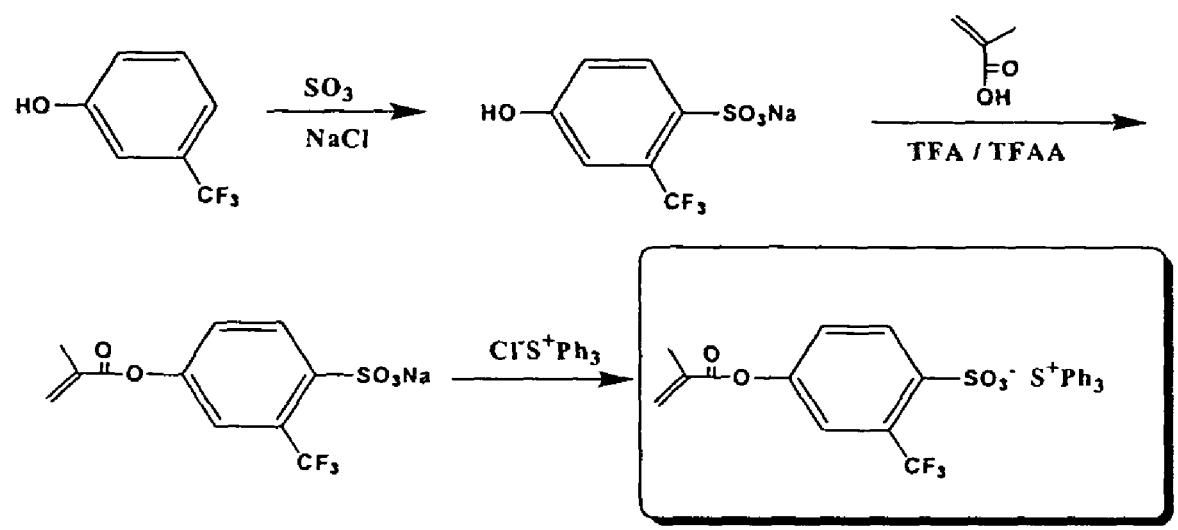
FIG. 6 illustrates a reaction scheme for producing a photoacid generator according to an embodiment of the present invention.
Figure 7:
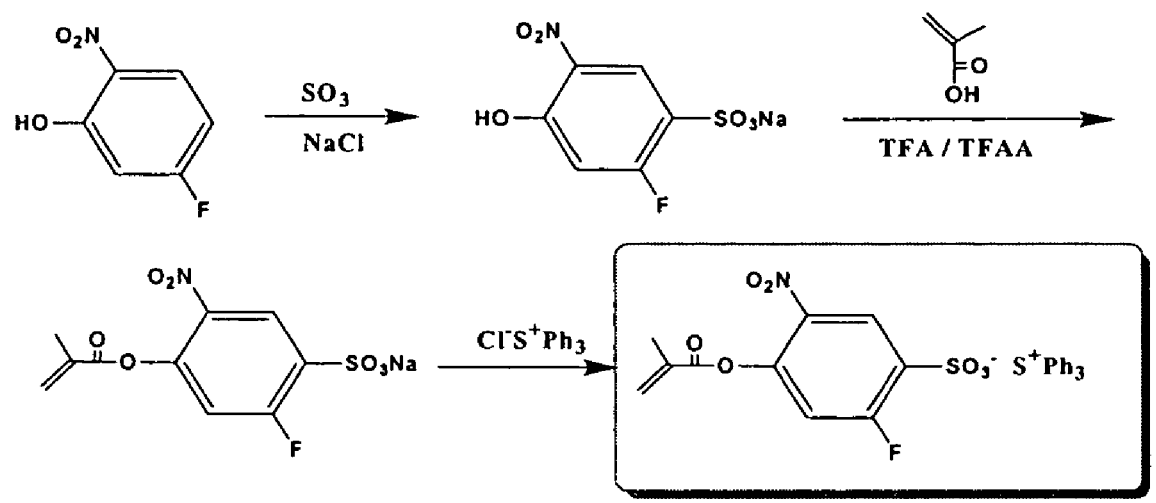
FIG. 7 illustrates a reaction scheme for producing a photoacid generator according to an embodiment of the present invention.
Figure 8:
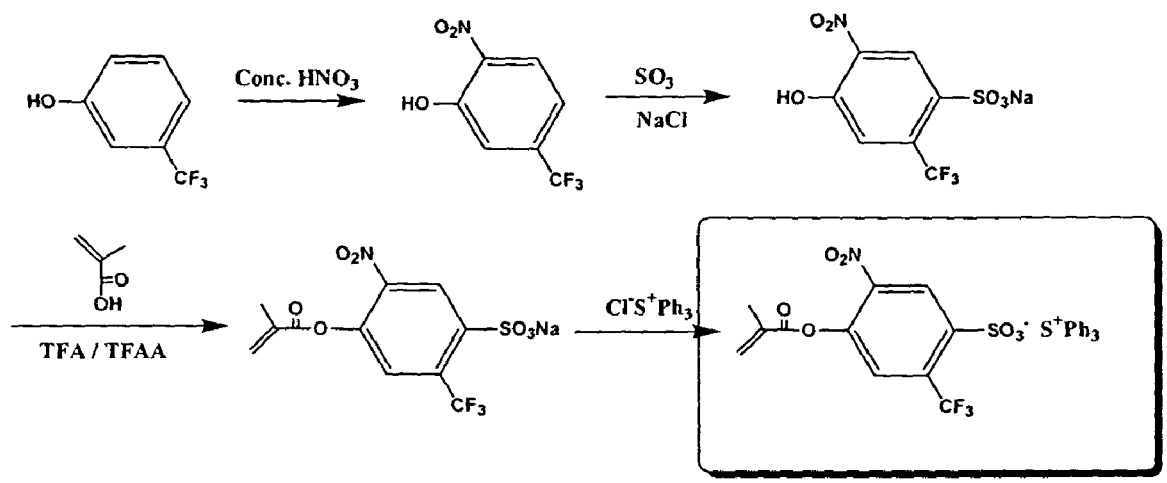
FIG. 8 illustrates a reaction scheme for producing a photoacid generator according to an embodiment of the present invention.

The present invention provides photoacid generators and lithographic resists comprising photoacid generators which can achieve high sensitivity, high contrast, high resolution, and/or high dry etch resistance for pattern transfer to a substrate. Moreover, the present invention provides photoacid generators and resists that address compatibility problems associated with photoacid generators which can lead to phase separation, non-uniform acid distribution, and non-uniform acid migration occurring during temperature fluctuations.

Definitions

In order to more clearly define the terms used herein, the following definitions are provided.

The terms alkyl, alkylene, alkenyl, alkenylene, alkynyl, and alkylene are intended to encompass straight chain and branched structures. The chemical nomenclature used herein is meant to be interpreted by one of skill in the art, and, therefore, any deviations and combinations of this type of nomenclature is also within the abilities of those of skilled in the art to interpret. Accordingly, this type of nomenclature is not to be applied to combinations that would result in an unrealistic molecule or substituent.

A resist, as used herein, refers to an imaging or recording medium, usually a polymeric material, that is used in a lithographic process, typically for the production of integrated circuits. In a general sense, a resist is a material that is used to prevent a particular chemical or physical reaction such as chemical attack, electrodeposition, vapor phase deposition, or other reactions. A resist of the present invention may comprise a positive resist or a negative resist.

Lithography, or a lithographic process, as used herein, refers to a process by which the pattern, typically a pattern of an integrated circuit, is imprinted onto a substrate or a resist. Lithography may be accomplished by exposing a recording medium with radiation of some form, followed by developing the pattern to be used, which results in the removal of either the exposed or the unexposed material. A variety of radiation sources may be used, including but not limited to, extreme ultraviolet (EUV) or deep ultraviolet (DUV) radiation, 193 nm radiation, X-rays, electron beams, and ion beams.

Photoacid Generators

In one embodiment, the present invention provides a photoacid generator of Formula (I):

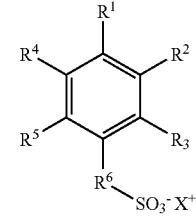

wherein $R^1$ is selected from the group consisting of -hydrogen, -alkyl, -alkenyl, -alkynyl, -cycloalkyl, -fluoroalkyl, -fluoroalkenyl, -fluoroalkynyl, -aryl, —O-alkyl, —O-alkenyl, —O-aryl, —O-alkylene-aryl, —O-alkylene-arylene-alkyl, —O-alkylene-arylene-alkenyl, —OC(O)-alkyl, —OC(O)-alkenyl, -carboxyl, and -hydroxyl, and wherein the alkenyl and the aryl groups of $R^1$ are optionally substituted 1 to 5 times with a substituent group, wherein the substituent group(s) are independently selected from the group consisting of -alkyl, -alkylene, -aryl, -carboxyl, and -hydroxyl.

$R^2$, $R^3$, $R^4$, and $R^5$ are independently selected from the group consisting of -hydrogen, -alkyl, -alkenyl, -fluoroalkyl, -fluoroalkenyl, —O-alkyl, -halo, -cyano, and -nitro.

R6 is a direct bond or selected from the group consisting of alkyl or fluorinated alkyl.

$X^+$ is selected from the group consisting of a sulfonium compound and an ionium compound.

Sulfonium compounds, according to some embodiments of the present invention, have the formula:

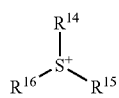

wherein $R^{14}$, $R^{15}$, and $R^{16}$ are independently selected from the group consisting of -alkyl and -aryl, wherein the aryl is optionally substituted 1 to 5 times with a substituent group, wherein the substituent group(s) are independently selected from the group consisting of -alkyl and -aryl.

Ionium compounds, according to some embodiments of the present invention, have the formula:

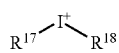

wherein $R^{17}$ and $R^{18}$ are independently selected from the group consisting of -alkyl and -aryl, wherein the aryl is optionally substituted 1 to 5 times with a substituent group, wherein the substituent group(s) are independently selected from the group consisting of -alkyl and -aryl.

Non-limiting examples of photoacid generators of Formula (I) are provided below:

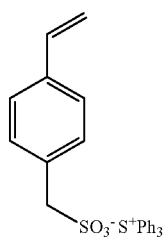
(PAG 1)

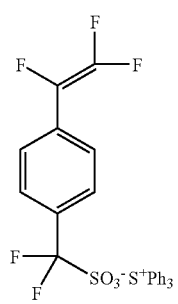
(PAG 2)

-continued

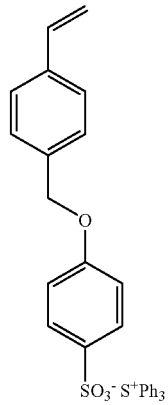
(PAG 3)

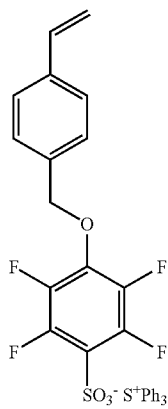
(PAG 4)

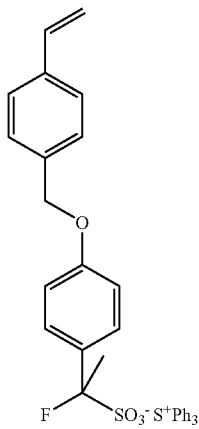
(PAG 5)

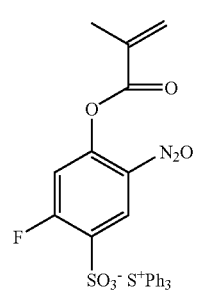
(PAG 6)

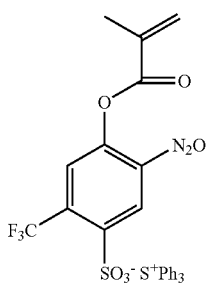

(PAG 7)

Photoacid generators of Formula (I), according to some embodiments of the present invention, are synthesized according to the reaction schemes illustrated in FIGS. 1-8.

In another embodiment, the present invention provides a photoacid generator of Formula (II):

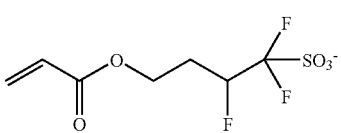

wherein $R^1$ is selected from the group consisting of alkylene, alkenylene, fluorinated alkylene, and fluorinated alkenylene; and $X^+$ is selected from the group consisting of a sulfonium compound and an ionium compound.

Sulfonium and ionium compounds, in some embodiments of photoacid generators of Formula (II), are consistent with the sulfonium and ionium compounds provided in Formula (I).

A non-limiting example of a photoacid generator of Formula (II) is provided below:

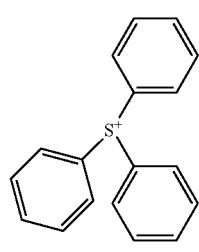

PAG 8

Figure 9:
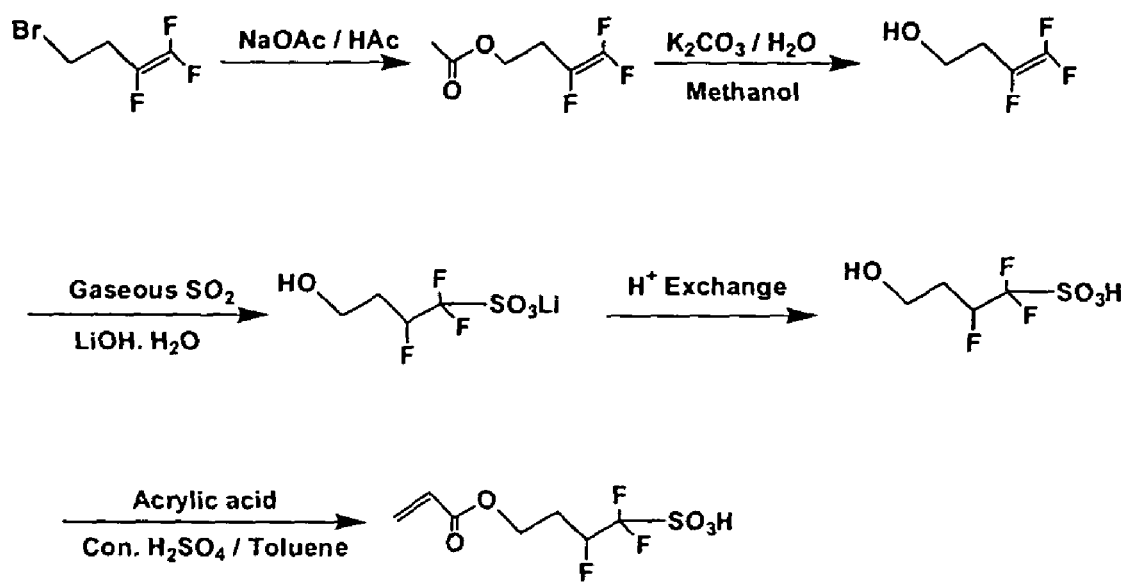
FIG. 9 illustrates a reaction scheme for producing a photoacid generator according to an embodiment of the present invention.

Photoacid generators of Formula (II), in some embodiments, are synthesized according to the reaction scheme provided in FIG. 9.

In another embodiment, the present invention provides a photoacid generator of Formula (III):

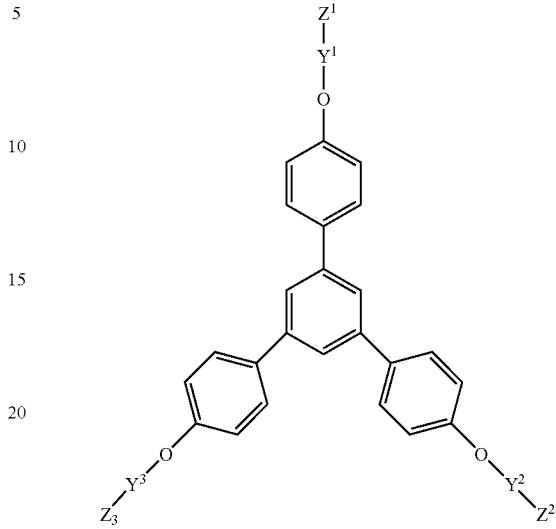

wherein $Y^1$, $Y^2$, and $Y^3$ are independently selected from the group consisting of alkylene, alkenylene, fluoroalkylene, and fluoroalkenylene.

$Z^1$, $Z^2$, and $Z^3$ are independently selected from the group consisting of:

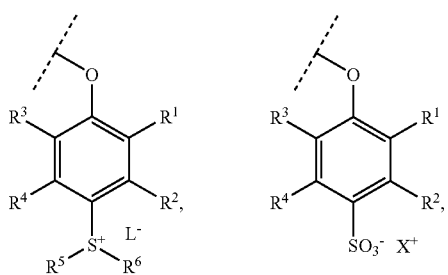

and —O—C(O)—O—$R^7$ wherein $R^1$, $R^2$, $R^3$, $R^4$, $R^5$, and $R^6$ are independently selected from the group consisting of -hydrogen, -alkyl, -alkylene, -fluoroalkyl, -fluoroalkenyl, -aryl, -substituted aryl, —O-alkyl, -halo, -cyano, and -nitro; and wherein $R^7$ is selected from the group consisting of -hydrogen, -alkyl, -alkenyl, -fluoroalkyl, -fluoroalkenyl, -pyranyl, and -adamantyl.

$L^-$ is selected from the group consisting of a sulfonate compound, $BF_4^-$, $PF_6^-$, and $SbF_6^-$; and $X^+$ is selected from the group consisting of a sulfonium compound or an ionium compound.

Sulfonium and ionium compounds, in some embodiments of photoacid generators of Formula (III), are consistent with the sulfonium and ionium compounds provided in Formula (I). Moreover, sulfonate compounds, in some embodiments of photoacid generators of Formula (III), comprise $^-OSO_2C_4F_9$ and/or $^-OSO_2CF_3$.

Non-limiting examples of photoacid generators of Formula (III) are provided below:

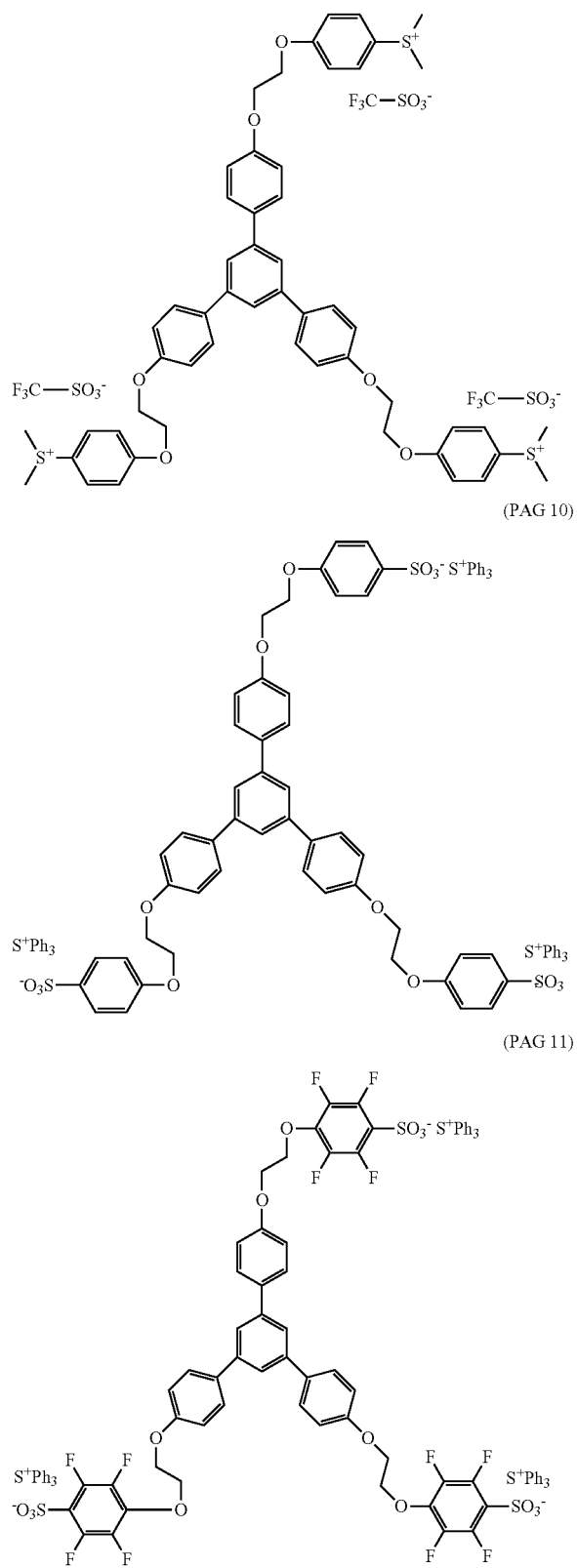

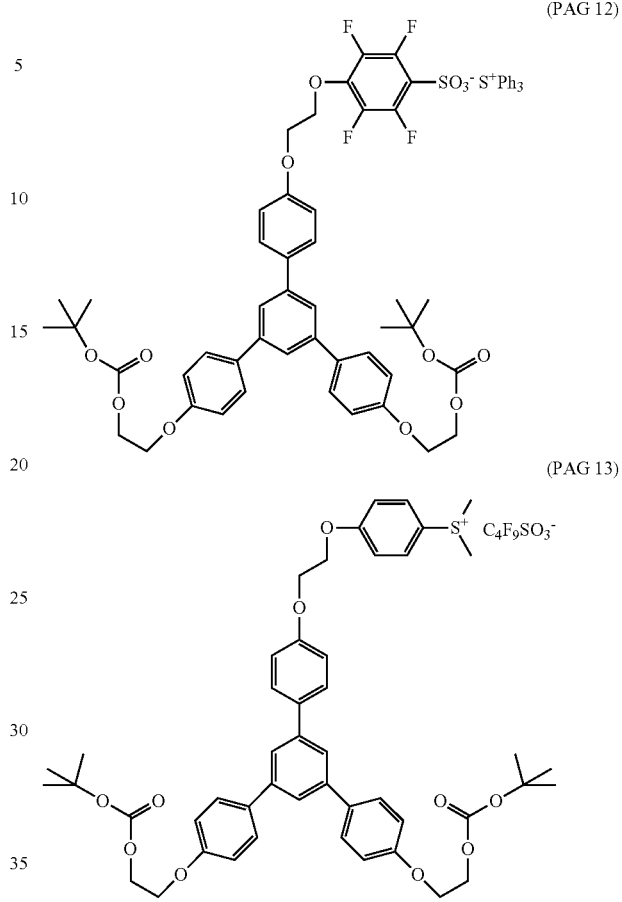

Figure 10:
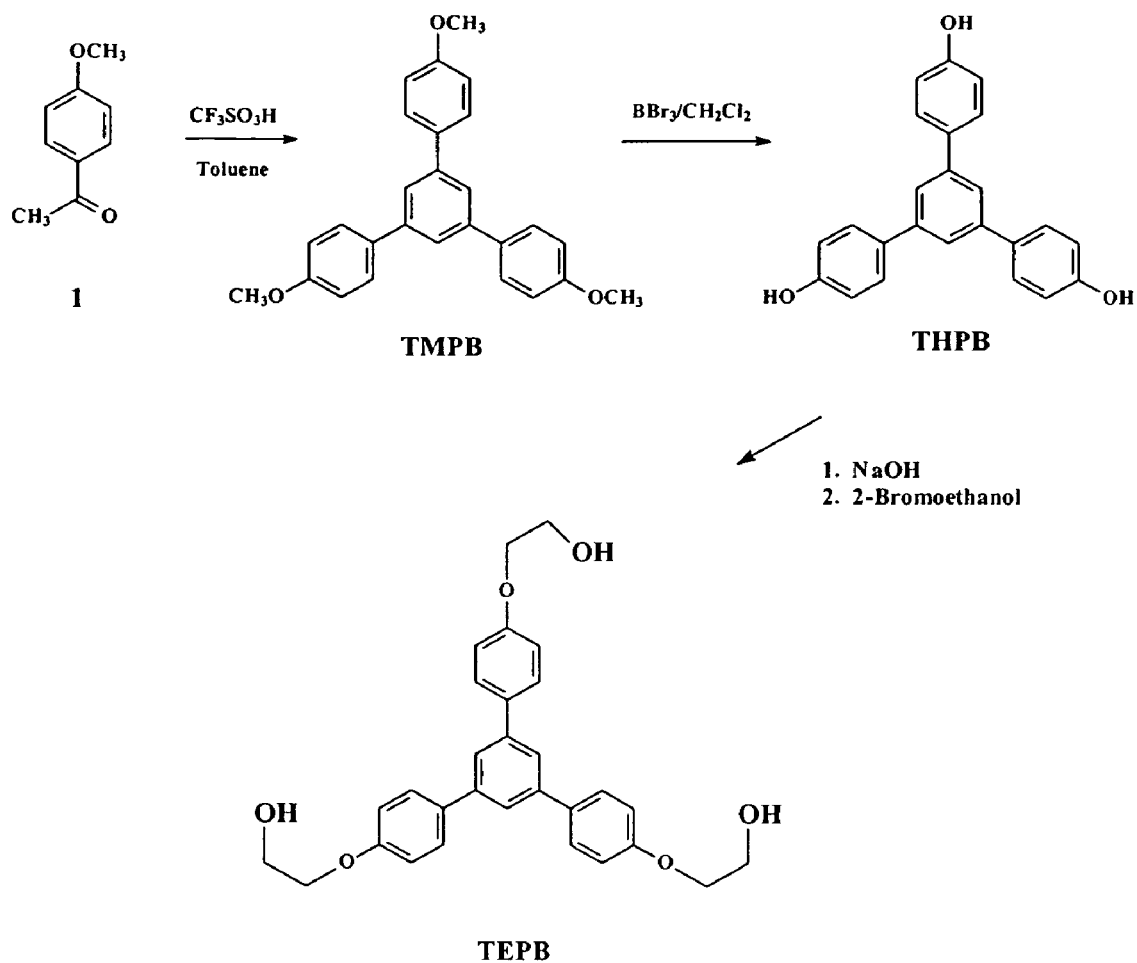
FIG. 10 illustrates a reaction scheme for producing a photoacid generator according to an embodiment of the present invention.
Figure 11:
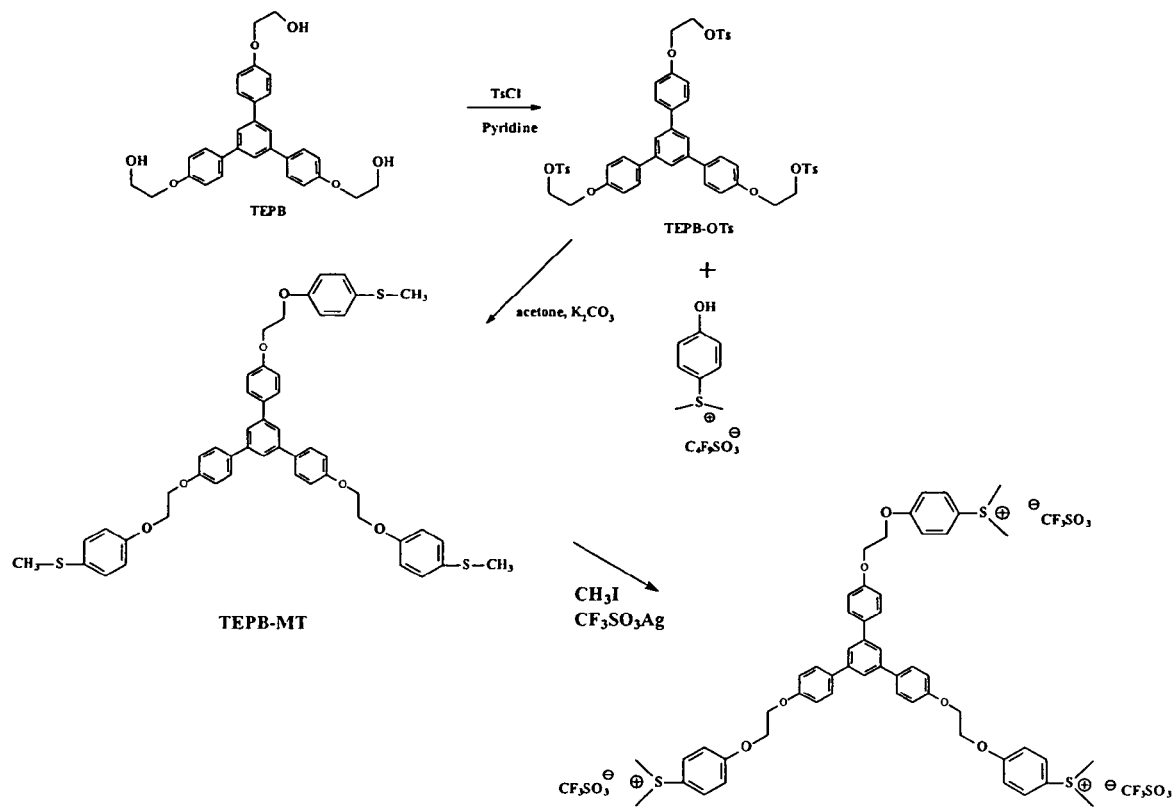
FIG. 11 illustrates a reaction scheme for producing a photoacid generator according to an embodiment of the present invention.
Figure 12:
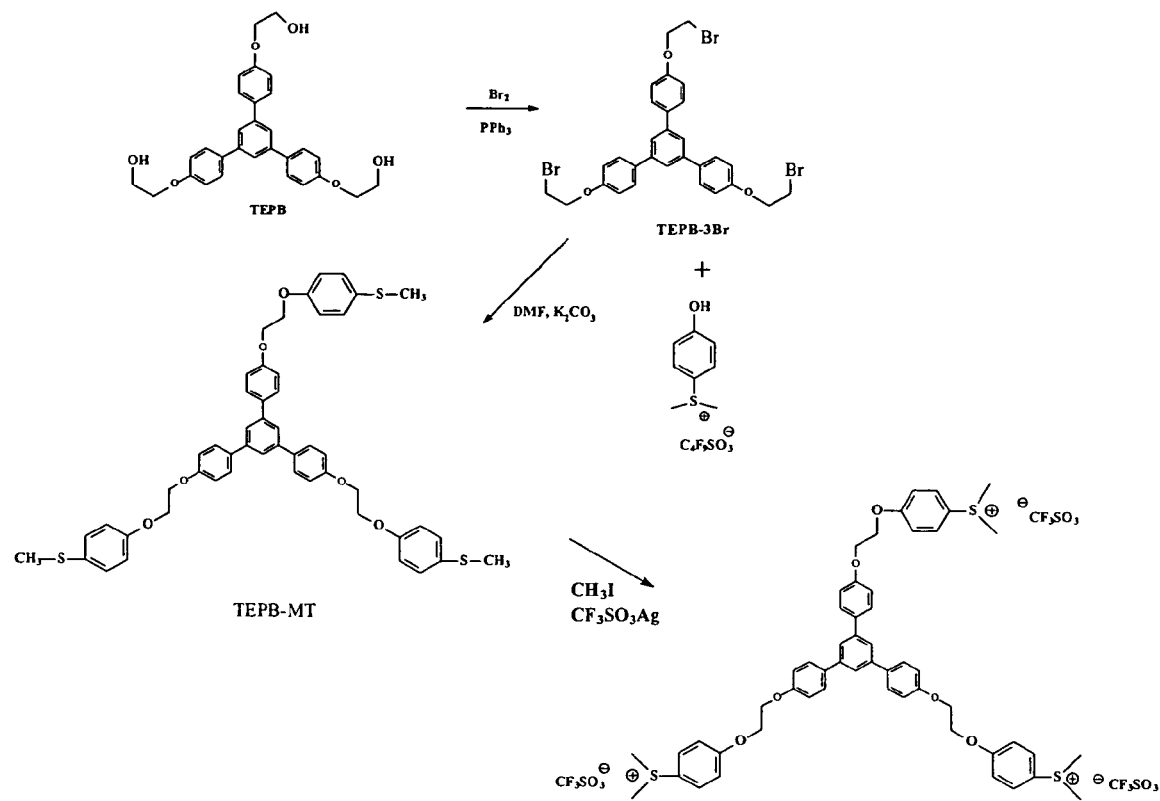
FIG. 12 illustrates a reaction scheme for producing a photoacid generator according to an embodiment of the present invention.
Figure 13:
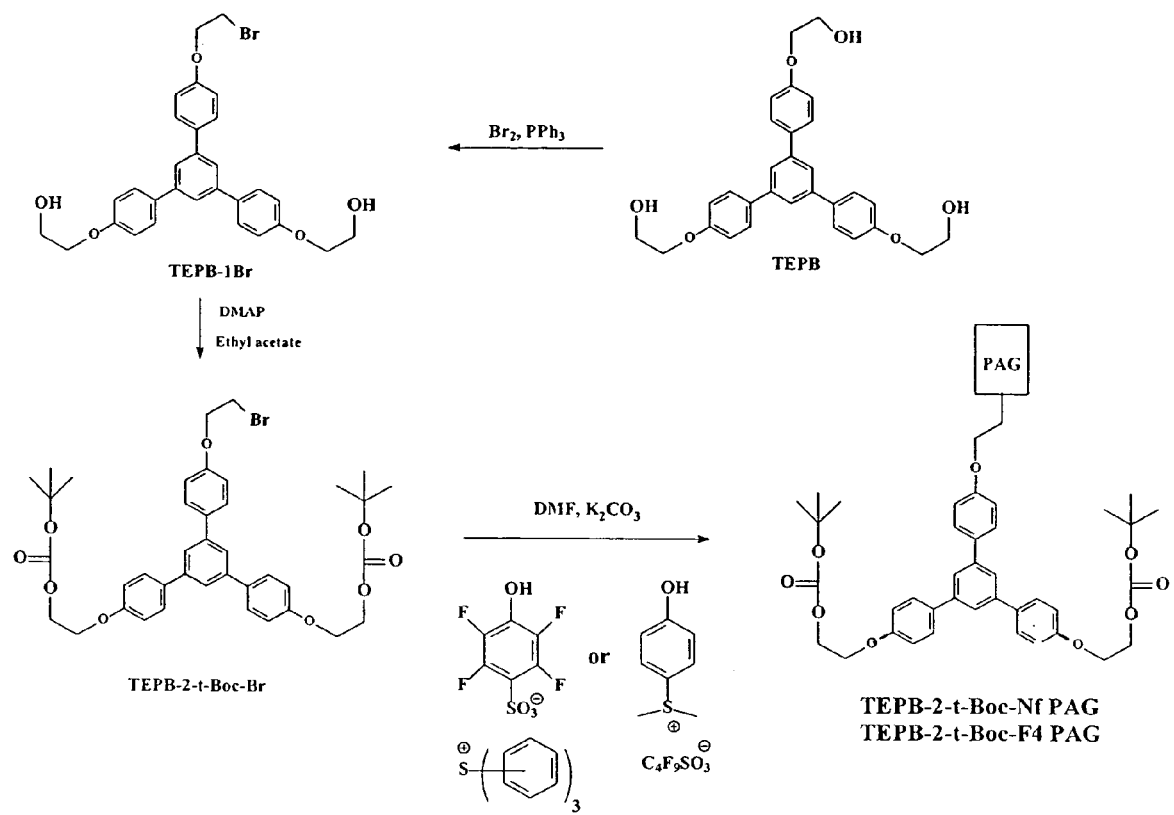
FIG. 13 illustrates a reaction scheme for producing a photoacid generator according to an embodiment of the present invention.

Photoacid generators of Formula (III), in some embodiments, are synthesized according to the reaction schemes provided in FIGS. 10-13. The reaction scheme of FIG. 10 illustrates synthesis of the core of a photoacid generator of Formula (III) according to an embodiment of the present invention. Once produced, the 1,3,5-tris(methoxyphenyl)-benzene (TMPB) core, in some embodiments, is reacted with subsequent reagents according to the reaction schemes of FIGS. 11, 12, and 13 to produce various photoacid generators of Formula (III).

In a further embodiment, the present invention provides a dendrimer comprising at least one photoacid generating moiety. In some embodiments, a dendrimer comprises a plurality of photoacid generating moieties. In addition to at least one or a plurality of photoacid generating moieties, a dendrimer, in some embodiments, comprises at least one acid labile protecting group.

In one embodiment, the present invention provides a dendrimer comprising at least one acid labile protecting group and no photoacid generating moieties. In another embodiment, the present invention provides a dendrimer comprising a plurality of acid labile protecting groups and no photoacid generating moieties.

Dendrimers comprising photoacid generating moieties and/or acid labile protecting groups, according to some embodiments of the present invention, comprise zero generation (G0), first generation (G1), second generation (G2), third generation (G3), fourth generation (G4), fifth generation (G5), and greater than fifth generation (G5) dendrimers.

In some embodiments, the present invention provides a dendrimer of Formula (IV):

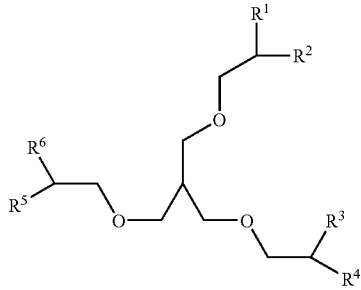

wherein $R^1$, $R^2$, $R^3$, $R^4$, $R^5$, and $R^6$ are independently selected from the group consisting of:

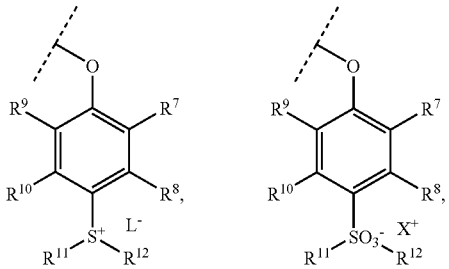

and —O—C(O)—O—$R^{13}$
  wherein $R^7$, $R^8$, $R^9$, $R^{10}$, $R^{11}$, and $R^{12}$ are independently selected from the group consisting of -hydrogen, -alkyl, -alkylene, -fluoroalkyl, -fluoroalkenyl, -aryl, -substituted aryl, —O-alkyl, -halo, -cyano, and -nitro; and
  wherein $R^{13}$ is selected from the group consisting of -hydrogen, -alkyl, -alkenyl, -fluoroalkyl, -fluoroalkenyl, -pyranyl, and -adamantyl.
  $L^-$ is selected from the group consisting of a sulfonate compound, $BF_4^-$, $PF_6^-$, and $SbF_6^-$; and
  $X^+$ is selected form the group consisting of a sulfonium compound and an ionium compound.

Sulfonium and ionium compounds, in some embodiments of dendrimers of Formula (IV), are consistent with the sulfonium and ionium compounds provided in Formula (I). Moreover, sulfonate compounds, in some embodiments of photoacid generators of Formula (IV), comprise $^-OSO_2C_4F_9$ and/or $^-OSO_2CF_3$.

In some embodiments, dendrimers of Formula (IV) are synthesized according to the reaction scheme illustrated in FIG. 14.

Lithographic Resists Comprising Photoacid Generators

In another aspect, the present invention provides lithographic resists comprising photoacid generators and/or dendrimers as described herein. In one embodiment, the present invention provides a resist comprising at least one photoacid generator of Formula (I). In another embodiment, the present invention provides a resist comprising at least one photoacid generator of Formula (II). In another embodiment, the present invention provides a resist comprising at least one photoacid generator of Formula (III). A polymeric resist, in some embodiments, comprises a plurality of photoacid generators of Formula (I), Formula (II), and/or Formula (III). In a further embodiment, the present invention provides a lithographic resist comprising at least one dendrimer of Formula (IV).

In one embodiment, the present invention provides a polymeric resist comprising an adamantyl component and a photoacid generating component, wherein the photoacid generating component comprises at least one photoacid generator of Formula (I), Formula (II), and/or Formula (III). In some embodiments, the photoacid generating component comprises a plurality of photoacid generators of Formula (I), Formula (II), and/or Formula (III). Moreover, in some embodiments, a polymeric resist comprising an adamantyl component and a photoacid generating component further comprises a hydroxystyrene component or a γ-butyrolactone component.

In some embodiments, the adamantyl component of a polymeric resist comprises methyl-adamantyl methacrylates, ethyl-adamantyl methacrylates, such as 2-ethyl-2-adamantyl methacrylate, propyl-adamantyl methacrylates, butyl-adamantyl methacrylates, methoxybutyl-adamantyl methacrylates, such as 2-(4-methoxybutyl)-2-adamantyl methacrylate, hydroxy-adamantyl methacrylates, such as 3-hydroxy-adamantyl methacrylate, or combinations thereof. Moreover, a hydroxystyrene component of a polymeric resist, in some embodiments, comprises para-hydroxystyrene (PHS), poly-(para-hydroxystyrene) (poly-PHS), or combinations thereof. In some embodiments, a γ-butyrolactone component comprises a γ-butryolactone methacrylate.

Figure 15:
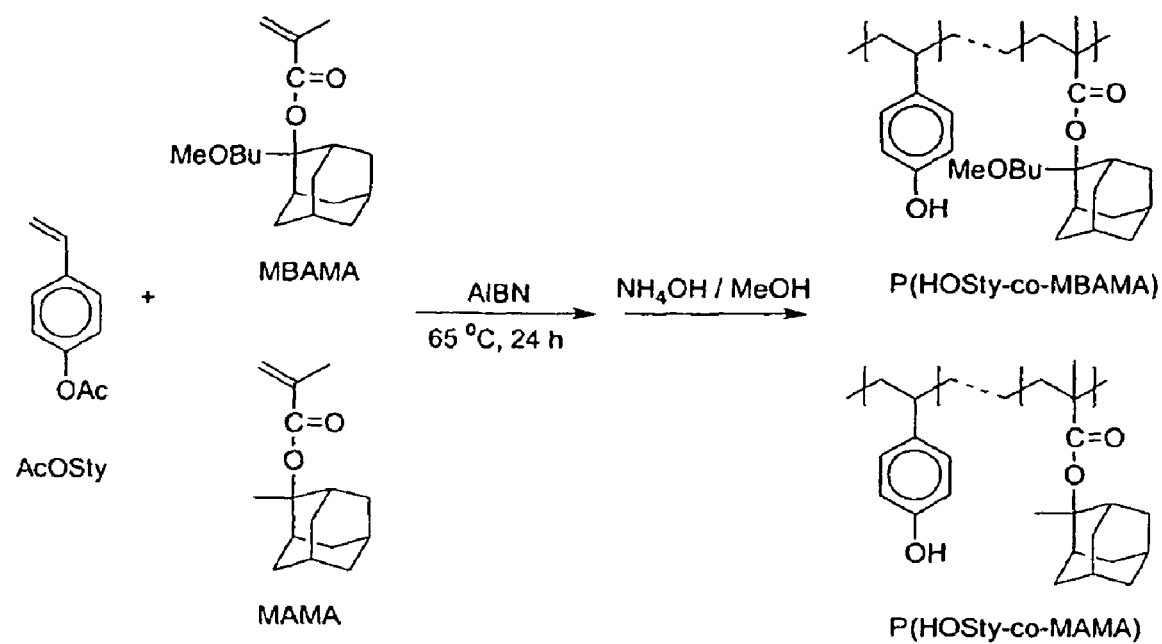
FIG. 15 illustrates copolymerization of a hydroxystyrene component and an adamantyl component according to embodiments of the present invention.
Figure 16:
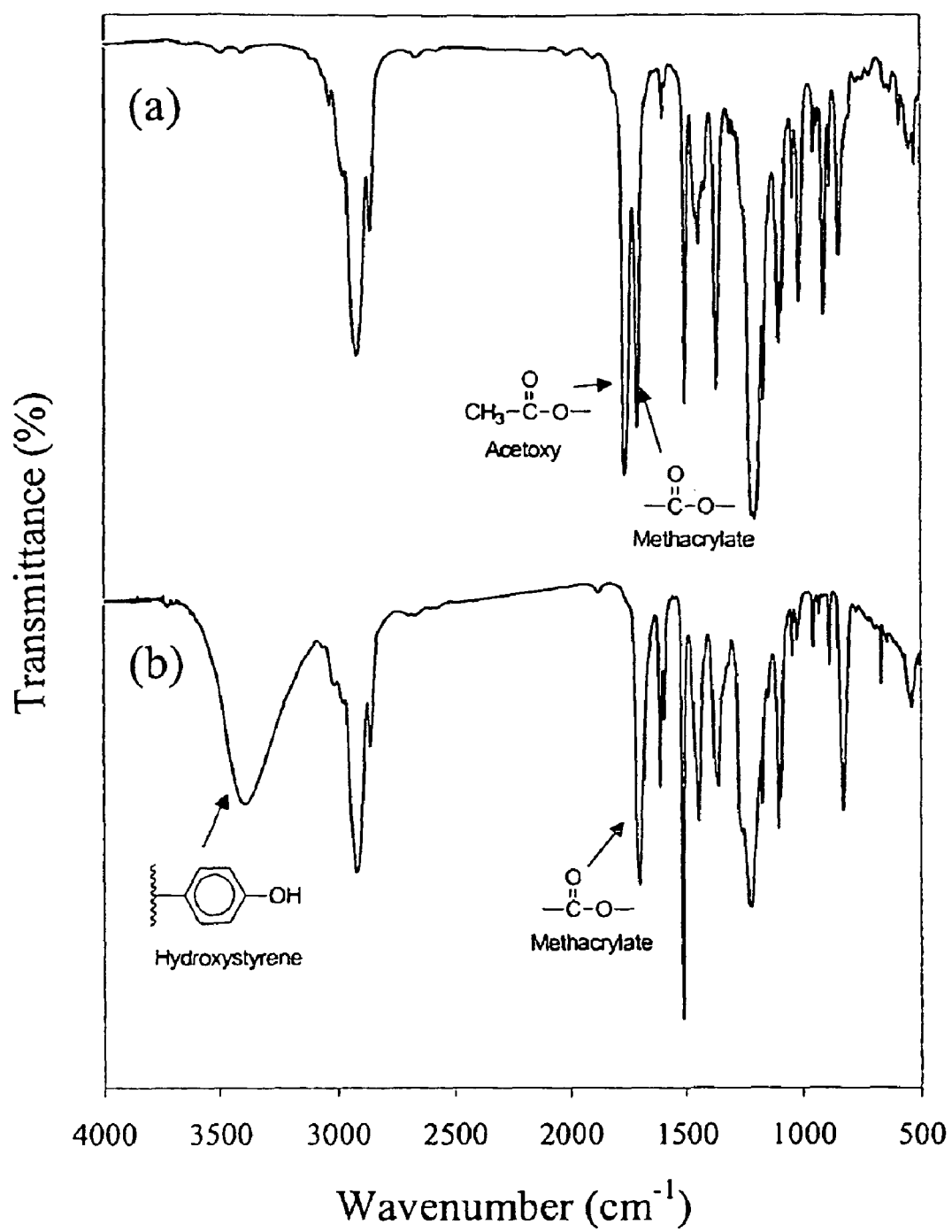
FIG. 16 is a FT-IR spectrum of a polymeric resist comprising a hydroxystyrene component copolymerized with an adamantyl component according to an embodiment of the present invention.

In some embodiments, the adamantyl component and hydroxystyrene component of the resist are copolymerized. FIG. 15 illustrates copolymerization of an adamantyl component and hydroxystyrene component in the production of a polymeric resist according to an embodiment of the present invention. FIG. 16 illustrates an FT-IR spectrum of a polymeric resist comprising an adamantyl component copolymerized with a hydroxystyrene component according to an embodiment of the present invention.

In some embodiments, a copolymer of a hydroxystyrene component and an adamantyl component comprises about 45 mol % hydroxystyrene component and about 55 mol % adamantyl component. In other embodiments, a copolymer of a hydroxystyrene component and an adamantyl component comprises about 40 mol % hydroxystyrene component and about 60 mol % adamantyl component. In a further embodiment, a copolymer of a hydroxystyrene component and an adamantyl component comprises about 20 mol % hydroxystyrene component and about 80 mol % adamantyl component.

In some embodiments, a copolymer of a hydroxystyrene component and an adamantyl component comprises from about 10 mol % to about 50 mol % hydroxystyrene component. In other embodiments, a copolymer of a hydroxystyrene component and an adamantyl component comprises from about 20 mol % to about 40 mol % hydroxystyrene component.

In some embodiments, the weight average molecular weight ($M_w$) of a copolymer of a hydroxystyrene component and an adamantyl component ranges from about 2200 to about 8000. In some embodiments, the glass transition ($T_g$) temperature of a copolymer of a hydroxystyrene component and an adamantyl component ranges from about 100° C. to about 170° C. In other embodiments, the glass transition temperature ranges from about 100° C. to about 120° C.

Figure 17:
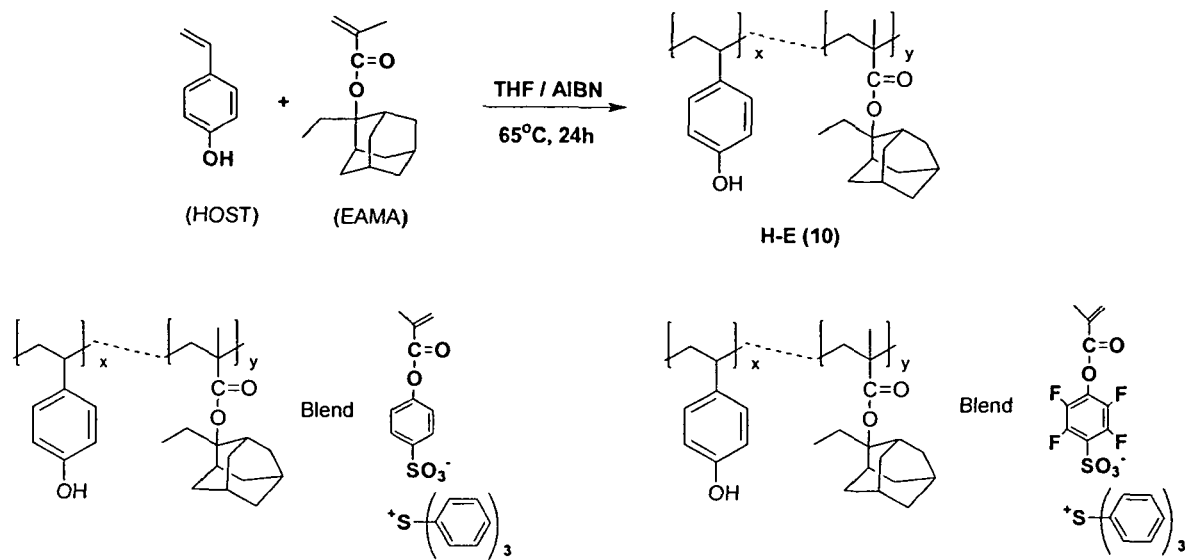
FIG. 17 illustrates a synthetic scheme for a polymeric resist according to an embodiment of the present invention.

A photoacid generating component, in some embodiments, is blended with a copolymer comprising a hydroxystyrene component and an adamantyl component in producing a polymeric resist of the present invention. In some embodiments, the blended photoacid generating component comprises at least one photoacid generator of Formula (I), Formula (II), and/or Formula (III). In other embodiments, the blended photoacid generating component comprises a plurality of photoacid generators of Formula (I), Formula (II), and/or Formula (III). FIG. 17 provides a synthetic scheme for a polymeric resist comprising a copolymer of a hydroxystyrene component and an adamantyl component and a blended photoacid generating component according to one embodiment of the present invention. In the reaction scheme, hydroxystyrene is copolymerized with 2-ethyl-2-adamantyl methacrylate. The resulting copolymer is blended with a photoacid generator of Formula (I) comprising triphenylsulfonium salt 4-(methacryloxy)benzenesulfonate (MBS-TPS) and/or triphenylsulfonium salt 4-(methacryloxy) 2,3,5,6-tetrafluorobenzenesulfonate (F4-MBS-TPS).

In some embodiments, the blended photoacid generating component comprises from about 1 weight percent to about 20 weight percent of the polymeric resist. In other embodiments, the blended photoacid generating component comprises from about 5 weight percent to about 15 weight percent of the polymeric resist. In a further embodiment, the blended photoacid generating component comprises about 10 weight percent of the polymeric resist.

In some embodiments, a polymeric resist comprising a hydroxystyrene component, an adamantyl component, and a blended photoacid generating component can further comprise a base component. The base component, in some embodiments, is blended into the polymer matrix. Base components operable to be blended into the polymer matrix, in some embodiments, comprise triethyl amine, trioctyl amine, tetramethyl ammonium hydroxide, and tetrabutyl ammonium hydroxide.

Figure 18:
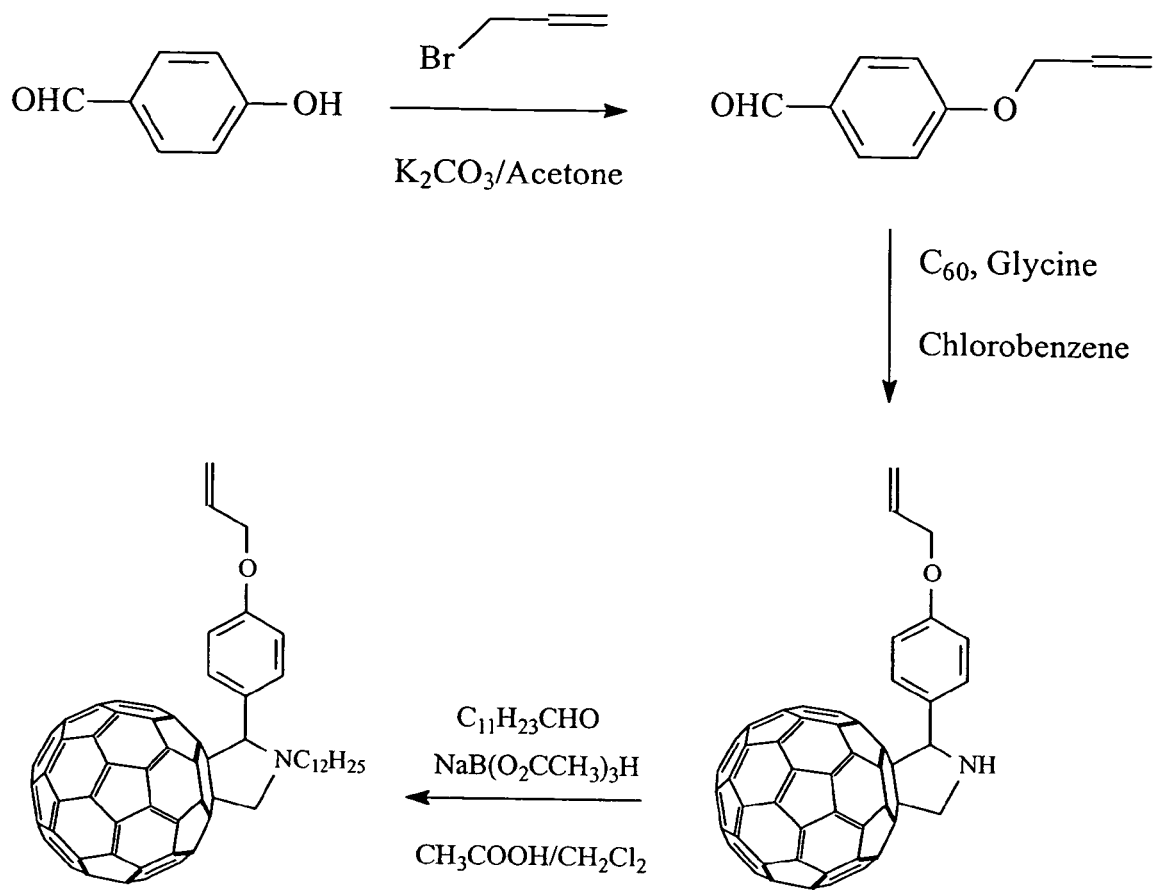
FIG. 18 illustrates a reaction scheme for a fullerene derivative according to an embodiment of the present invention.

In some embodiments, a polymeric resist comprising a hydroxystyrene component, an adamantyl component, and a blended photoacid generating component can further comprise a fullerene component. The fullerene component, in some embodiments, can be blended into the polymer matrix. Fullerene components operable to be blended into the polymer matrix, in some embodiments, comprise fullerene derivatives as illustrated in FIG. 18.

Figure 19:
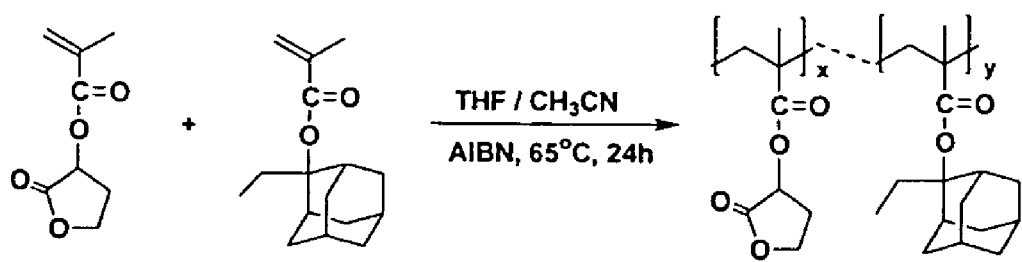
FIG. 19 illustrates copolymerization of a γ-butyrolactone component and an admantyl component according to an embodiment of the present invention.

In another embodiment, the present invention provides a polymeric resist comprising an adamantyl component copolymerized with a γ-butyrolactone component. FIG. 19 illustrates copolymerization of an adamantyl component and γ-butyrolactone component according to an embodiment of the present invention.

In some embodiments, a copolymer of a γ-butyrolactone component and an adamantyl component comprises about 60 mol % γ-butyrolactone component and about 40 mol % adamantyl component. In other embodiments, a copolymer of a γ-butyrolactone component and an adamantyl component comprises about 65 mol % γ-butyrolactone component and about 35 mol % adamantyl component. In a further embodiment, a copolymer of a γ-butyrolactone component and an adamantyl component comprises about 50 mol % γ-butyrolactone component and about 50 mol % adamantyl component.

In some embodiments, a copolymer of a γ-butyrolactone component and an adamantyl component comprises from about 30 mol % to about 70 mol % γ-butyrolactone component. In other embodiments, a copolymer of a γ-butyrolactone component and an adamantyl component comprises from about 40 mol % to about 60 mol % γ-butyrolactone component.

In some embodiments, the weight average molecular weight ($M_w$) of a copolymer of a γ-butyrolactone component and an adamantyl component ranges from about 2200 to about 8000. In some embodiments, the glass transition ($T_g$) temperature of a copolymer of a γ-butyrolactone component and an adamantyl component ranges from about 100° C. to about 150° C. In other embodiments, the glass transition temperature ranges from about 100° C. to about 120° C.

A photoacid generating component, in some embodiments, is blended with a copolymer comprising a γ-butyrolactone component and an adamantyl component in producing a polymeric resist of the present invention. In some embodiments, the blended photoacid generating component comprises at least one photoacid generator of Formula (I), Formula (II), and/or Formula (III). In other embodiments, the blended photoacid generating component comprises a plurality of photoacid generators of Formula (I), Formula (II), and/or Formula (III). FIG. 20 provides a synthetic scheme for a polymeric resist comprising a copolymer of a γ-butyrolactone component and an adamantyl component and a blended photoacid generating component according to one embodiment of the present invention. In the reaction scheme, γ-butyrolactone is copolymerized with 2-ethyl-2-adamantyl methacrylate. The resulting copolymer is blended with a photoacid generator of Formula (I) comprising triphenylsulfonium salt 4-(isobutyloxy)benzenesulfonate (IBBS-TPS) and/or triphenylsulfonium salt 4-(isobutyloxy) 2,3,5,6-tetrafluorobenzenesulfonate (F4-IBBS-TPS).

In some embodiments, the blended photoacid generating component comprises from about 1 weight percent to about 20 weight percent of the polymeric resist. In other embodiments, the blended photoacid generating component comprises from about 5 weight percent to about 15 weight percent of the polymeric resist. In a further embodiment, the blended photoacid generating component comprises about 10 weight percent of the polymeric resist.

In some embodiments, a polymeric resist comprising a γ-butyrolactone component, an adamantyl component, and a blended photoacid generating component can further comprise a base component. The base component, in some embodiments, is blended into the polymer matrix. Base components operable to be blended into the polymer matrix, in some embodiments, comprises triethyl amine, trioctyl amine, tetramethyl ammonium hydroxide, and tetrabutyl ammonium hydroxide.

In some embodiments, a polymeric resist comprising a γ-butyrolactone component, an adamantyl component, and a blended photoacid generating component can further comprise a fullerene component. The fullerene component, in some embodiments, is blended into the polymer matrix. Fullerene components operable to be blended into the polymer matrix, in some embodiments, comprise fullerene derivatives such as those illustrated in FIG. 18.

Lithographic Resist with Photoacid Generating Groups Incorporated in the Resist Chains In another aspect, the present invention provides polymeric resists comprising photoacid generators incorporated into the polymeric resist chains as part of the polymeric unit. In one embodiment, the present invention provides a polymeric resist comprising at least one photoacid generator of Formula (I) incorporated into the polymeric chain of the resist. In another embodiment, the present invention provides a polymeric resist comprising at least one photoacid generator of Formula (II) incorporated into the polymeric chain of the resist. In another embodiment, the present invention provides a polymeric resist comprising at least one photoacid generator of Formula (III) incorporated into the polymeric chain of the resist. In a further embodiment, a polymeric resist comprises a plurality of photoacid generators of Formula (I), Formula (II), and/or Formula (III) incorporated into the polymeric chain of the resist.

In one embodiment, a polymeric resist comprising at least one photoacid generator incorporated in the polymeric resist chain comprises an adamantyl component and a photoacid generating component. In some embodiments, the adamantyl component comprises an adamantyl methacrylate. Adamantyl methacrlyates, in some embodiments, comprise ethyl-adamantyl methacrylates, such as 2-ethyl-2-adamantyl methacrylate, propyl-adamantyl methacrylates, butyl-adamantyl methacrylates, methoxybutyl-adamantyl methacrylates, such as 2-(4-methoxybutyl)-2-adamantyl methacrylate, hydroxy-adamantyl methacrylates, such as 3-hydroxy-adamantyl methacrylate, or combinations thereof.

The photoacid generating component incorporated into the polymeric resist chain, in some embodiments, comprises at least one photoacid generator of Formula (I), Formula (II), and/or Formula (III). In some embodiments, the photoacid generating component incorporated into the polymeric resist chain comprises a plurality of photoacid generators of Formula (I), Formula (II), and/or Formula (III).

Figure 21:
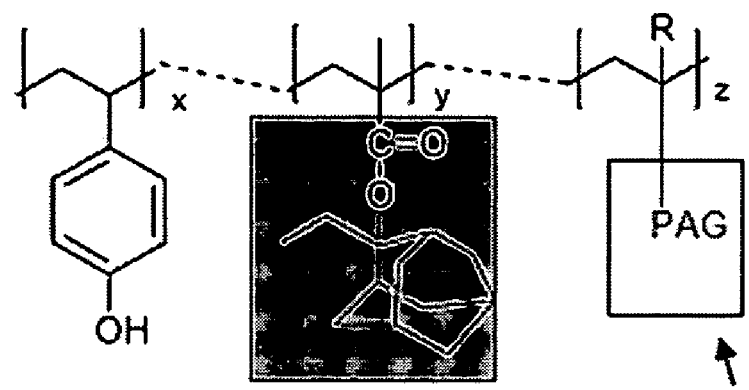
FIG. 21 illustrates a synthetic scheme for a polymeric resist according to an embodiment of the present invention.

Polymeric resists comprising an adamantyl component and a photoacid generating component incorporated into the polymeric resist chain, in some embodiments, further comprise a hydroxystyrene component. A hydroxystyrene component, in some embodiments, comprises para-hydroxystyrene (PHS), poly-(para-hydroxystyrene) (poly-PHS), or combinations thereof. FIG. 21 illustrates a polymeric resist comprising a hydroxystyrene component, an adamantyl component, and a photoacid generating component incorporated into the polymeric resist chain.

Photoacid generators of Formula (I), Formula (II), and/or Formula (III) incorporated in the polymeric resist chain, according to embodiments of the present invention, comprise a polymerizable functionality permitting copolymerization with the adamantyl and hydroxystyrene components.

In some embodiments, a polymeric resist comprising a hydroxystyrene component, an adamantyl component, and a photoacid generating component incorporated into the polymeric resist chain comprises about 35 mol % hydroxystyrene component, about 50 mol % adamantyl component, and about 15% photoacid generating component. In some embodiments, the hydroxystyrene component content of the polymeric resist ranges from about 20 mol % to about 50 mol % or from about 30 mol % to about 40 mol %. The adamantyl component content of the polymeric resist, in some embodiments, ranges from about 25 mol % to about 60 mol % or from about 30 mol % to about 50 mol %. The photoacid generating component content of the polymeric resist, in some embodiments, ranges from about 1 mol % to about 30 mol %, from about 5 mol % to about 20 mol %, or from about 10 mol % to about 15 mol %.

Figure 22:
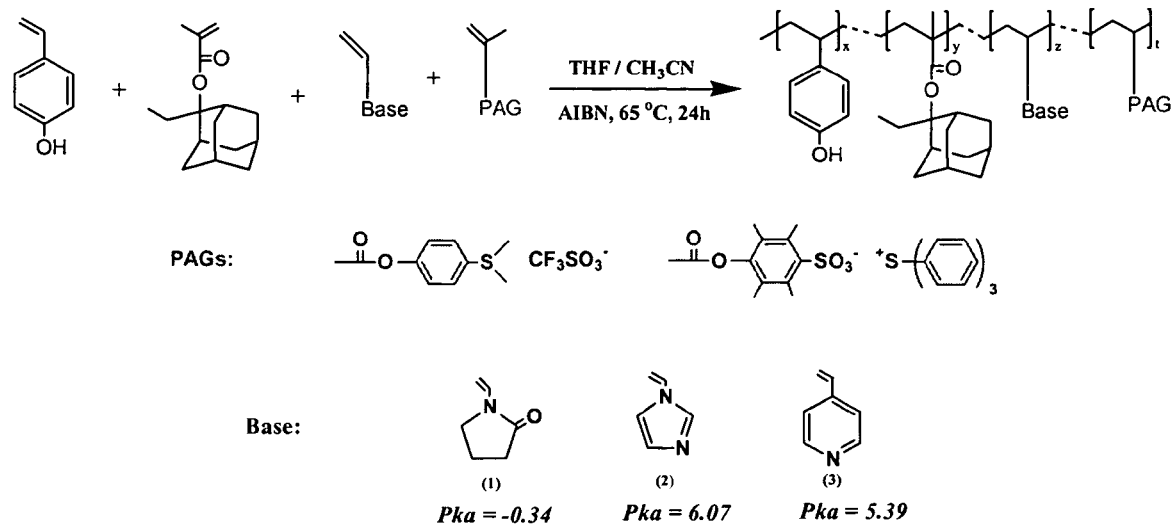
FIG. 22 illustrates a synthetic scheme for a polymeric resist according to an embodiment of the present invention.

A base component, in some embodiments, can be incorporated in the polymeric chain of a polymeric resist comprising a hydroxystyrene component, an adamantyl component, and a photoacid generating component. Incorporation of a base component into the polymeric resist chain, in some embodiments, is effectuated according to the reaction scheme provided in FIG. 22. Base components operable to be incorporated into the polymeric chain of the polymeric resist, in some embodiments, can comprise N-vinylpyrrolidone and other bases with polymerizable functionalities. Base components, according to embodiments of the present invention, can be operable to control acid diffusion and concomitantly enhance resolution.

In some embodiments, a fullerene component can be incorporated in the polymeric chain of a polymeric resist comprising a hydroxystyrene component, an adamantyl component, and a photoacid generating component. Fullerene components operable to be incorporated in the polymeric chain, in some embodiments, comprise fullerene derivatives as illustrated in FIG. 18.

In some embodiments, the weight average molecular weight ($M_w$) of a polymeric resist comprising a hydroxystyrene component, an adamantyl component, and a photoacid generating component incorporated in the polymeric resist chain ranges from about 1900 to about 6000. In some embodiments, the weight average molecular weight ($M_w$) ranges from about 2500 to about 5000 or from about 3000 to about 4000.

Figure 23:
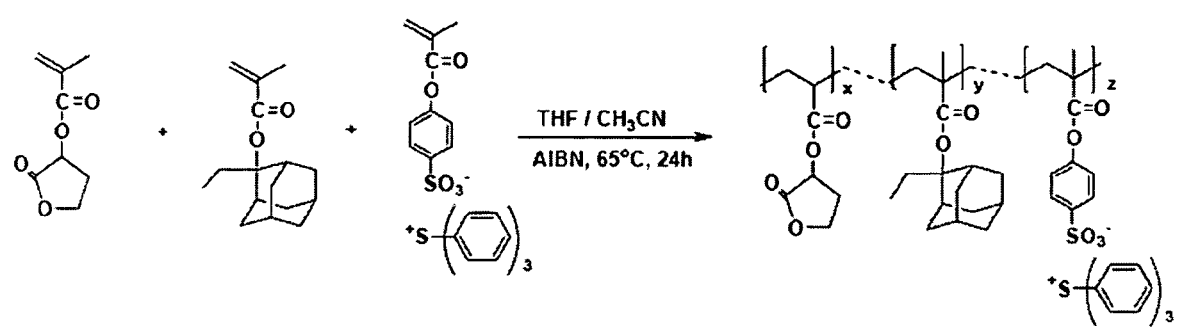
FIG. 23 illustrates a synthetic scheme for a polymeric resist according to an embodiment of the present invention.
Figure 24:
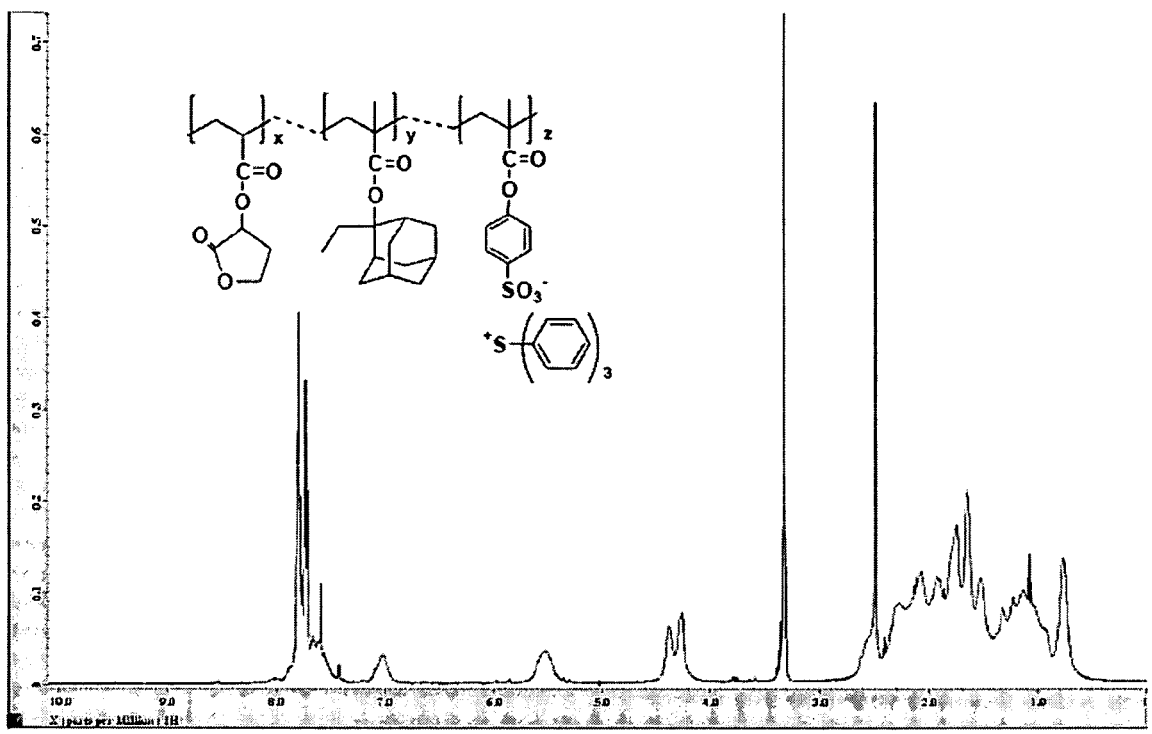
FIG. 24 is a $^1$H NMR spectrum of a polymeric resist according to an embodiment of the present invention.

Polymeric resists comprising an adamantyl component and a photoacid generating component incorporated into the polymeric resist chain as provided herein, in some embodiments, further comprises a γ-butyrolactone component. The γ-butyrolactone component, in some embodiments, is copolymerized with the adamantyl component and photoacid generating component. In some embodiments, the γ-butyrolactone component comprises γ-butyrolactone methacrylate. Polymeric resists comprising a γ-butyrolactone component, adamantyl component, and photoacid generating component can be synthesized, in some embodiments, according to the reaction scheme illustrated in FIG. 23. FIG. 24 provides a $^1$H NMR spectrum of a polymeric resist comprising a γ-butyrolactone component, an adamantyl component, and a photoacid generating component according to an embodiment of the present invention.

In some embodiments, a polymeric resist comprising a γ-butyrolactone component, an adamantyl component, and a photoacid generating component incorporated into the polymeric resist chain comprises about 45 mol % γ-butyrolactone component, about 40 mol % adamantyl component, and about 15% photoacid generating component. In some embodiments, the γ-butyrolactone component content of the polymeric resist ranges from about 25 mol % to about 60 mol % or from about 30 mol % to about 50 mol %. The adamantyl component content of the polymeric resist, in some embodiments, ranges from about 25 mol % to about 50 mol % or from about 30 mol % to about 40 mol %. The photoacid generating component content of the polymeric resist, in some embodiments, ranges from about 1 mol % to about 30 mol %, from about 5 mol % to about 20 mol %, or from about 10 mol % to about 15 mol %.

A base component, in some embodiments, can be incorporated in the polymeric chain of a polymeric resist comprising a γ-butyrolactone component, an adamantyl component, and a photoacid generating component. Base components operable to be incorporated into the polymeric backbone of the polymeric resist, in some embodiments, can comprise N-vinylpyrrolidone and other bases with polymerizable functionalities. Base components, according to embodiments of the present invention, can be operable to control acid diffusion and concomitantly enhance resolution.

In some embodiments, the weight average molecular weight ($M_w$) of a polymeric resist comprising a γ-butyrolactone component, an adamantyl component, and a photoacid generating component incorporated in the polymeric resist chain ranges from about 1900 to about 6000. In some embodiments, the weight average molecular weight ($M_w$) ranges from about 2500 to about 5000 or from about 3000 to about 4000.

In another aspect the present invention provides methods for producing lithographic resists. In one embodiment, a method for producing a resist comprises blending a photoacid generating component with a first component, wherein the photoacid generating component comprises at least one photoacid generator of Formula (I), Formula (II), and/or Formula (III). In some embodiments, the photoacid generating component comprises a plurality of photoacid generators of Formula (I), Formula (II), and/or Formula (III). In some embodiments, the first component comprises an adamantyl component as provided herein. A method for producing a lithographic resist, in some embodiments, further comprises blending a photoacid generating group with a second component in addition to the first component. A second component, in some embodiments, comprises a hydroxystyrene component or a γ-butyrolactone component. In one embodiment, the first component and second component are copolymerized. Copolymerization of the first and second components, in some embodiments, is completed prior to blending with the photoacid generating component.

A method for producing a lithographic resist, in another embodiment, comprises copolymerizing a first component and a photoacid generating component, wherein the photoacid generating component comprises at least one photoacid generator of Formula (I), Formula (II), and/or Formula (III). In some embodiments, the photoacid generating component comprises a plurality of photoacid generators of Formula (I), Formula (II), and/or Formula (III). The first component, in some embodiments, comprises a first monomer, first oligomer, and/or first polymer. In one embodiment, the first component comprises an adamantyl component.

In some embodiments, a method for producing a lithographic resist further comprises copolymerizing a second component with the first component and photoacid generating component. The second component, in some embodiments, comprises a second monomer, second oligomer, and/or second polymer. In one embodiment, the second component comprises a hydroxystyrene component or a γ-butyrolactone component.

Lithographic Processes

The present invention also provides lithographic processes comprising exposing a lithographic recording medium to radiation to form a pattern and developing the pattern, wherein the lithographic recording medium comprises any resist of the present invention described herein. In some embodiments, the radiation of lithographic processes of the present invention comprises extreme ultraviolet radiation, 193 nm, X-ray radiation, electron beam radiation, ion beam radiation, or combinations thereof. Additionally, lithographic processes of the present invention can be used to produce integrated circuits.

Embodiments of the present invention are further illustrated in the following Examples.

Synthesis of Photoacid Generators

EXAMPLE 1

Synthesis of Triphenylsulfonium salt 4-vinylbenzylsulfonate (VBzS-TPS)

P-chloromethylstyrene (20 mmol) in 10 ml acetone was added dropwise to the aqueous solution of sodium sulfite (25 mmol) under nitrogen at reflux, and the mixture was refluxed for 12 hours. After cooling to room temperature, the solid was filtered and washed with water, acetone, and dried under high vacuum overnight to give pure product sodium salt, 4-vinyl benzylsulfonate (F4-VBzS-Na) as white solid in 81% yield. characterized by $^1$H NMR (25° C., ppm) δ7.34 (d, J=9.1 Hz, 2H); 7.26 (d, J=9.1 Hz, 2H); 6.72 (dd, J=10.7 and 18.6 Hz, 1H); 5.79 (d, J=18.6 Hz, 1H); 5.20 (d, J=10.7 Hz, 3H); 3.68 (s, 3H). Then the (VBzS-Na) was reacted with triphenylsulfonium chloride 50% aqueous solution in water, at room temperature overnight. The product was refined with dichloromethane and hexane, Triphenylsulfonium salt 4-vinylbenzylsulfonate (VBzS-TPS) was obtained in 90% yield as a colorless crystal. $^1$H NMR (25° C., ppm) δ7.42-7.92 (m, 15H); 7.32 (d, J=8.7 Hz, 2H); 7.24 (d, J=8.7 Hz, 2H); 6.68 (dd, J=11.2 and 18.0 Hz, 1H); 5.75 (d, J=18.0 Hz, 1H); 5.17 (d, s J=11.2 Hz, 3H); 3.66 (s, 3H).

EXAMPLE 2

Synthesis of Triphenylsulfonium salt 4-(vinyl benzyloxy) benzenesulfonate (VBzBS-TPS)

P-chloromethylstyrene (20 mmol) in 10 ml acetone was added dropwise to the aqueous solution of sodium 4-hydroxy-2.3.5.6-tetrafluoro benzenesulfonate (25 mmol) under nitrogen at reflux, and the mixture was refluxed for 12 hours. After cooling to room temperature, the solid was filtered and washed with acetone, and dried under high vacuum overnight to give pure product sodium salt, 4-(vinyl benzyloxy) benzenesulfonate (VBzBS-Na) as white solid in 76% yield. characterized by $^1$H NMR (25° C., ppm) δ7.46-7.54 (m, 4H); 7.41 (d, J=9.0 Hz, 2H); 6.93 (d, J=9.3 Hz, 2H); 6.72 (dd, J=11.0 and 18.4 Hz, 1H); 5.83 (d, J=18.4 Hz, 1H); 5.27 (d, J=11.0 Hz, 1H); 5.1 (s, 2H). Then the (VBzBS-Na) was reacted with triphenylsulfonium chloride 50% aqueous solution in water, at room temperature overnight. The product was refined with dichloromethane and hexane, triphenylsulfonium salt 4-(vinyl benzyloxy) benzenesulfonate (VBzBS-TPS) was obtained in 90% yield as a colorless crystal. $^1$H NMR (25° C., ppm) δ7.39-7.90 (m, 21H); 6.92 (d, J=9.1 Hz, 2H); 6.73 (dd, J=11.0 and 18.2 Hz, 1H); 5.82 (d, J=18.2 Hz, 1H); 5.25 (d, s J=11.0 Hz, 1H); 5.1 (s, 2H).

EXAMPLE 3

Synthesis of Triphenylsulfonium salt 4-(vinyl benzyloxy) 2,3,5,6-tetrafluoro benzenesulfonate (F4-VBzBS-TPS)

P-chloromethylstyrene (20 mmol) in 10 ml acetone was added dropwise to the aqueous solution of sodium 4-hydroxy-2.3.5.6-tetrafluoro benzenesulfonate (25 mmol) under nitrogen at reflux, and the mixture was refluxed for 12 hours. After cooling to room temperature, the solid was filtered and washed with water and acetone, and dried under high vacuum overnight to give pure product sodium salt, 4-(vinyl benzyloxy) 2.3.5.6-tetrafluoro benzenesulfonate (F4-VBzBS-Na) as white solid in 79% yield. characterized by $^1$H NMR (25° C., ppm) δ7.49 (d, J=8.1 Hz, 2H); 7.41 (d, J=8.1 Hz, 2H); 6.72 (dd, J=11.2 and 17.8 Hz, 1H); 5.85 (d, J=17.8 Hz, 1H); 5.26 (d, s J=11.2 Hz, 3H), $^{19}$F NMR (25° C., ppm, ext.CF$_3$COOH): δ −152.15 (m, 2F); −137.45 (m, 2F). Then the (F4-VBzBS-Na) was reacted with triphenylsulfonium chloride 50% aqueous solution in water, at room temperature overnight. The product was refined with dichloromethane and hexane, triphenylsulfonium salt 4-(vinyl benzyloxy) 2.3.5.6-tetrafluoro benzenesulfonate (F4-VBzBS-TPS) was obtained in 90% yield as a colorless crystal. $^1$H NMR (25° C., ppm) δ7.42-7.92 (m, 19H); 6.73 (dd, J=11.2 and 17.8 Hz, 1H); 5.86 (d, J=17.8 Hz, 1H); 5.27 (d, s J=11.2.0 Hz, 3H).

EXAMPLE 4

Synthesis of Triphenylsulfonium salt 4-vinylbenzylsulfonate (VBzS-TPS)

Triphenylsulfonium salt 4-vinylbenzylsulfonate (VBzS-TPS) was prepared as set forth in Example 1. To a solution of hexamethyldisilazane (1 mL) in THF(10 mL) was added Bu-Li(1.5 mL) at −78° C. After 1 hour at −78° C., The solution was dropwise added to a solution of VBzS-TPS (0.6 g) and N-fluorophenylsulfonimide(0.95 g)in DMF and THF cosolvents(10 mL) at −78° C. After 3 hours at −78° C., the resulting solution was warmed to ambient temperature and allowed to react an additional 3 hours. The reaction was quenched with saturated brine, extracted with dichloromethane and washed with water, to dried and removed the solvents to give a pale brown oil, in 33% yield. $^1$H NMR (25° C., ppm) δ7.02-8.13 (m, 19H). $^{13}$C NMR (25° C., ppm) δ 162.8, 152.0, 141.2, 140.8, 138.2, 136.3, 134.5, 133.1, 132.5, 131.3, 130.4, 129.5, 128.4, 127.0, 126.3, 125.4, 124.2 and 30.9. $^{19}$F NMR (25° C., ppm, ext. CF$_3$COOH): δ −97.55 (m, 2F); −38.07 (m, 1F); 38.55 (m, 1F); 50.20 (m, 1F).

EXAMPLE 5

Synthesis of Triphenylsulfonium salt 4-(methacryloxy) 2,3,5,6-tetrafluoro benzenesulfonate (F4-MBS-TPS)

First, 4-hydroxy-2.3.5.6-tetrafluoro benzenesulfonate was prepared as per literature method[10]. This was then reacted with methacrylic acid in trifluoroacetic acid (TFA) and trifluoroacetic anhydride (TFAA) as media[11], under a nitrogen atmosphere overnight, to get sodium 4-(methacryloxy) 2.3.5.6-tetrafluorobenzenesulfonate [F4-MBS-Na] in 97% yield, characterized by $^1$H NMR (25° C., ppm) δ6.45 (s, 1H); 6.13 (s, 1H); 2.06 (s, 3H), $^{19}$F NMR (25° C., ppm, ext.CF$_3$COOH): δ −152.35 (m, 2F); −137.68 (m, 2F). Then the F4-MBS-Na was reacted with triphenylsulfonium chloride 50% aqueous solution in water, at room temperature overnight. The product was refined with dichloromethane and hexane, F4-MBS-TPS was obtained in 90% yield as a colorless crystal, MP: 57-59° C. $^1$H NMR (25° C., ppm) δ7.42-

7.92 (m, 15H); 6.45 (s, 1H); 6.12 (s, 1H); 2.03 (s, 3H). $^{13}$C NMR (25° C., ppm) δ162.8, 141.0, 136.3, 134.5, 133.1, 132.5, 131.3, 130.4, 128.7, 125.4, 124.2 and 17.9. $^{19}$F NMR (25° C., ppm, ext. CF$_3$COOH): δ −152.55 (m, 2F); −137.62 (m, 2F). Anal. Calcd for C$_{28}$H$_{20}$F$_4$O$_5$S$_2$: C, 58.33; H, 3.50; F, 13.18; O, 13.87; S, 11.12. Found: C, 58.39; H, 3.34; F, 12.85; O, 13.83; S, 11.06.

EXAMPLE 6

Synthesis of Triphenylsulfonium salt 4-(methacryloxy) benzenesulfonate (MBS-TPS)

Triphenylsulfonium salt 4-(methacryloxy) benzenesulfonate (MBS-TPS) was prepared by a similar procedure to that of F4-MBS-TPS above by reacting sodium 4-phenosulfonate and methacrylic acid in TFA and TFAA media, yield 88% as a colorless crystal, MP: 68-70° C. $^1$H NMR (25° C., ppm) δ7.61-7.82 (m, 17H); 7.09 (d, J=8.0 Hz, 2H); 6.28 (s, 1H); 5.89 (s, 1H) and 2.00 (s, 3H). $^{13}$C NMR (25° C., ppm) δ 165.3, 150.4, 146.2, 141.0, 135.2, 134.5, 132.5, 131.4, 127.9, 126.9, 125.2, 121.1 and 18.0. Anal. Calcd for C$_{28}$H$_{24}$O$_5$S$_2$: C, 66.64; H, 4.79; O, 15.85; S, 12.71. Found: C, 66.77; H, 4.44; O, 15.65; S, 12.35.

EXAMPLE 7

Synthesis of Triphenylsulfonium salt 4-(vinyl) benzenesulfonate (VBS-TPS)

Triphenylsulfonium salt 4-(vinyl) benzenesulfonate (VBS-TPS) was prepared by reacting sodium 4-styrenesulfonate and triphenylsulfonium chloride 50% aqueous solution in water, at room temperature overnight, yield 83% as a colorless crystal[12], MP: 56-58° C. $^1$H NMR (25° C., ppm) δ7.65-7.92 (m, 15H); 7.54 (d, J=8.1 Hz, 2H); 7.40 (d, J=8.1 Hz, 2H); 6.72 (dd, J=17.6 and 10.8 Hz, 1H); 5.84 (d, J=17.6 Hz, 1H) and 5.26 (d, J=10.8 Hz, 1H). $^{13}$C NMR (25° C., ppm) δ148.0, 141.0, 137.1, 136.3, 134.5, 132.5, 131.4, 125.4, 124.2 and 114.7. Anal. Calcd for C$_{26}$H$_{22}$O$_3$S$_2$: C, 69.93; H, 4.97; O, 10.75; S, 14.36. Found: C, 69.77; H, 4.89; O, 11.19; O, 11.19; S, 14.74.

EXAMPLE 8

Synthesis of Triphenylsulfonium salt 4-(isobutyloxy) benezenesulfonate (IBBS-TPS)

Triphenylsulfonium salt 4-(isobutyloxy) benezenesulfonate (IBBS-TPS) was prepared by a similar procedure for (MBS-TPS) above using isobutyric acid instead of methacrylic acid in 90.5% yield as a colorless crystal, MP: 76-78° C. $^1$H NMR (25° C., ppm) δ7.46-7.86 (m, 15H); 7.60 (d, J=7.6 Hz, 2H); 7.04 (d, J=7.6 Hz, 2H); 2.81 (heptet, J=7.4 Hz, 1H) and 1.23 (s, 6H). $^{13}$C NMR (25° C., ppm) δ175.0, 150.4, 146.0, 134.4, 132.4, 131.3, 126.8, 125.1, 124.1, 120.9, 33.3 and 18.6. Anal. Calcd for C$_{28}$H$_{26}$O$_5$S$_2$: C, 66.38; H, 5.17; O, 15.79; S, 12.66. Found: C, 66.26; H, 4.70; O, 15.68; S, 13.03.

EXAMPLE 9

Synthesis of Triphenylsulfonium salt 4-(isobutyloxy) 2,3,5,6-tetrafluorobenzenesulfonate (F4-IBBS-TPS)

Triphenylsulfonium salt 4-(isobutyloxy) 2,3,5,6-tetrafluorobenzenesulfonate (F4-IBBS-TPS) was prepared by a method similar to F4-MBS-TPS above using isobutyric acid instead of methacrylic acid in 78.0% yield as a colorless crystal, MP: 62-64° C. $^1$H NMR (25° C., ppm) δ7.42-7.95 (m, 15H); 3.02 (heptet, J=7.2 Hz, 1H) and 1.26 (s, 6H). $^{13}$C NMR (25° C., ppm) δ172.9, 140.9, 136.2, 134.3, 132.4, 131.3, 131.0, 128.6, 125.1, 124.1, 33.1 and 18.4. $^{19}$F NMR (25° C., ppm, ext.CF$_3$COOH): δ −153.82 (m, 2F); −138.73 (m, 2F). Anal. Calcd for C$_{28}$H$_{22}$F$_4$O$_5$S$_2$: C, 58.12; H, 3.83; F, 13.13; O, 13.83; S, 11.08. Found: C, 58.34; H, 3.56; F, 12.79; O, 13.54; S, 10.83.

Synthesis of Polymeric Resists Comprising Photoacid Generators

EXAMPLE 10

Synthesis of a Polymeric Resist Comprising a Terpolymer of Hydroxystyrene, 2-Ethyl-2-Adamantyl Methacrylate, and 4-(vinyl) benzenesulfonate (VBS-TPS)

4-(vinyl) benzene sulfonate (VBS-TPS) was prepared in accordance with Example 7. A terpolymer of hydroxystyrene, 2-ethyl-2-adamantyl methacrlyation, and 4-(vinyl) benzenesulfonate (VBS-TPS) was prepared by free radical polymerization in a sealed pressure vessel. Hydroxystyrene, 2-ethyl-2-adamantyl-methacrylate, VBS-TPS, and 2,2'-azobisisobutyronitrile (AIBN) as a free radical initiator (5 mol % to the monomers) were dissolved in freshly distilled anhydrous tetrahydrofuran (THF) and acetonitrile. Polymerization was performed at 65° C. for 24 hours. The polymer solution was precipitated into a large amount of diethyl ether or petroleum ether and dried under vacuum.

EXAMPLE 11

Synthesis of a Polymeric Resist Comprising a Terpolymer of Hydroxystyrene, 2-Ethyl-2-Adamantyl Methacrylate, and Triphenylsulfonium salt 4-(methacryloxy) benzenesulfonate (MBS-TPS)

Triphenylsulfonium salt 4-(methacryloxy) benzenesulfonate (MBS-TPS) was prepared in accordance with Example 6. A terpolymer of hydroxystyrene, 2-ethyl-2-adamantyl methacrlyation, and triphenylsulfonium salt 4-(methacryloxy) benzenesulfonate (MBS-TPS) was prepared by free radical polymerization in a sealed pressure vessel. Hydroxystyrene, 2-ethyl-2-adamantyl-methacrylate, MBS-TPS, and 2,2'-azobisisobutyronitrile (AIBN) as a free radical initiator (5 mol % to the monomers) were dissolved in freshly distilled anhydrous tetrahydrofuran (THF) and acetonitrile. Polymerization was performed at 65° C. for 24 hours. The polymer solution was precipitated into a large amount of diethyl ether or petroleum ether and dried under vacuum.

EXAMPLE 12

Synthesis of a Polymeric Resist Comprising a Terpolymer of Hydroxystyrene, 2-Ethyl-2-Adamantyl Methacrylate, and Triphenylsulfonium salt 4-(methacryloxy) 2,3,5,6-tetrafluoro benzenesulfonate (F4-MBS-TPS)

Triphenylsulfonium salt 4-(methacryloxy) 2,3,5,6-tetrafluoro benzenesulfonate (F4-MBS-TPS) was prepared in accordance with Example 5. A terpolymer of hydroxystyrene, 2-ethyl-2-adamantyl methacrlyation, and Triphenylsulfonium salt 4-(methacryloxy) 2,3,5,6-tetrafluoro benzenesulfonate (F4-MBS-TPS) was prepared by free radical polymerization in a sealed pressure vessel. Hydroxystyrene, 2-ethyl-2-adamantyl-methacrylate, F4-MBS-TPS, and 2,2'-azobisisobutyronitrile (AIBN) as a free radical initiator (5 mol % to the monomers) were dissolved in freshly distilled anhydrous tetrahydrofuran (THF) and acetonitrile. Polymerization was performed at 65° C. for 24 hours. The polymer solution was precipitated into a large amount of diethyl ether or petroleum ether and dried under vacuum.

Table I provides molar feed ratios and other chemical and physical properties of the polymeric resists synthesized in Examples 10-12.

TABLE I

Chemical and Physical Properties of Polymeric Resists

| Polymer | Mole Feed Ratio | | | Polymer Composition | | | | Mw* | Stability/ | Tg/ |
|---|---|---|---|---|---|---|---|---|---|---|
| (Resist) | HOST | EAMA | PAG | HOST | EAMA | PAG | Yield/% | (PDI) | °C. | °C. |
| EXAMPLE 10 HE-VBS-TPS | 30 | 65 | 5.0 | 41.7 | 48.6 | 9.7 | 44.3 | 3700 (1.7) | 156 | *** |
| EXAMPLE 11 HE-MBS-TPS | 25 | 73.5 | 1.5 | 37.7 | 55.8 | 6.5 | 35.4 | 3800 (1.8) | 153 | *** |
| EXAMPLE 12 HE-F4-MBS-TPS | 25 | 72.5 | 2.5 | 35.0 | 57.9 | 7.1 | 37.3 | 3600 (1.6) | 145 | *** |

EXAMPLE 13

Synthesis of a Polymeric Resist Comprising a Terpolymer of γ-Butyrolactone Methacrylate, 2-Ethyl-2-Adamantyl Methacrylate, and 4-(vinyl) benzenesulfonate (VBS-TPS)

4-(vinyl) benzene sulfonate (VBS-TPS) was prepared in accordance with Example 7. γ-Butyrolactone, 2-ethyl-2-adamantyl-methacrylate, VBS-TPS, and 2,2'-azobisisobutyronitrile (AIBN) as a free radical initiator (5 mol % to the monomers) were dissolved in freshly distilled anhydrous tetrahydrofuran (THF) and acetonitrile. Polymerization was performed at 65° C. for 24 hours. The polymer solution was precipitated into a large amount of diethyl ether or petroleum ether and dried under vacuum.

EXAMPLE 14

Synthesis of a Polymeric Resist Comprising a Terpolymer of γ-Butyrolactone Methacrylate, 2-Ethyl-2-Adamantyl Methacrylate, and Triphenylsulfonium salt 4-(methacryloxy) 2,3,5,6-tetrafluoro benzenesulfonate (F4-MBS-TPS)

Triphenylsulfonium salt 4-(methacryloxy) 2,3,5,6-tetrafluoro benzenesulfonate (F4-MBS-TPS) was prepared in accordance with Example 5. γ-Butyrolactone, 2-ethyl-2-adamantyl-methacrylate, F4-MBS-TPS, and 2,2'-azobisisobutyronitrile (AIBN) as a free radical initiator (5 mol % to the monomers) were dissolved in freshly distilled anhydrous tetrahydrofuran (THF) and acetonitrile. Polymerization was performed at 65° C. for 24 hours. The polymer solution was precipitated into a large amount of diethyl ether or petroleum ether and dried under vacuum.

Table II provides molar feed ratios and other chemical and physical properties of the polymeric resists synthesized in Examples 13-14.

Resist Processing

Polymeric resists of Examples 13 and 14 were processed according to the following procedure. 0.2 g of polymer prepared in accordance with Examples 13 or 14 was dissolved in 3.4 g of cyclohexanone. The resist solution was filtered through 0.2 μm filter and spin coated (2500 rpm, 60s) onto silicon wafers primed with a 20% 1,1,3,3,3-hexamethyldisilazane (HMDS)-80% propylene glycol-1-monomethylether-2-acetate (PGMEA) solution. The post apply bake was carried out at 100° C. for 90 seconds. The thickness of the resist was determined to be in the range of 110 nm to 150 nm. The exposed wafers were baked at 100 C for 90 s. The development was conducted in conventional 2.38-wt % tetramethylammonium hydroxide (TMAH) for approximately 10-20 s and rinsed with de-ionized water.

Lithographic Evaluation

Figure 25:
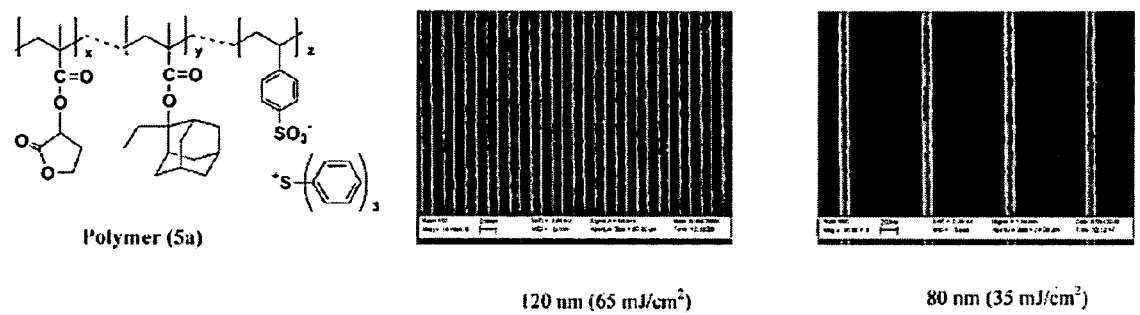
FIG. 25 provides scanning electron microscope images of a polymeric resist according to an embodiment of the present invention.

Exposed wafers were evaluated on an Raith 150 SEM. Top down SEM images of exposed polymeric resists of Examples 13 and 14 are provided in FIGS. 25 and 26 and the imaging properties are set forth in Table III. The polymeric resist of Example 14 (GE-F4-MBS-TPS) demonstrated 110 nm line/space at 11.5 mJ cm$^{-2}$ and 80 nm isolated features at 3.0 mJ cm$^{-2}$. The polymeric resist of Example 14 (GE-VBS-TBS) displayed a 120 nm line/space at 65 mJ cm$^{-2}$ and 80 nm isolated features at 35 mJ cm$^{-2}$.

Various embodiments of the invention have been described in fulfillment of the various objects of the invention. It should be recognized that these embodiments are merely illustrative of the principles of the present invention. Numerous modifications and adaptations will be readily apparent to those skilled in the art without departing from the spirit and scope of the present invention.

TABLE II

Chemical and Physical Properties of Polymeric Resists

| Polymer | Mole Feed Ratio | | | Polymer Composition | | | | Mw* | Stability/ | Tg/ |
|---|---|---|---|---|---|---|---|---|---|---|
| (Resist) | GBLMA | EAMA | PAG | GBLMA | EAMA | PAG | Yield/% | (PDI) | °C. | °C. |
| EXAMPLE 13 GE-VBS-TPS | 30.7 | 66.5 | 2.8 | 52.5 | 41.1 | 6.4 | 17.4 | 3700 (2.3) | 163 | 100 |
| EXAMPLE 14 GE-F4-MBS-TPS | 25 | 72.5 | 2.5 | 55.3 | 39.2 | 5.5 | 31.5 | 2100 (3.3) | 151 | 142 |

That which is claimed is:

1. A photoacid generator of Formula (III):

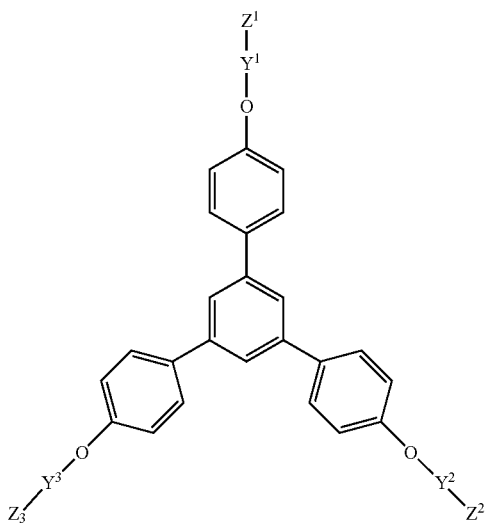

wherein
- $Y^1$, $Y^2$, and $Y^3$ are independently selected from the group consisting of alkylene, alkenylene, fluoroalkylene, and fluoroalkenylene;
- $Z^1$, $Z^2$, and $Z^3$ are independently selected from the group consisting of:

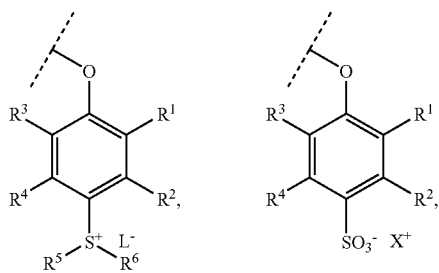

and —O—C(O)—O—$R^7$
- wherein $R^1$, $R^2$, $R^3$, $R^4$, $R^5$, and $R^6$ are independently selected from the group consisting of -hydrogen, -alkyl, -alkylene, -fluoroalkyl, -fluoroalkenyl, -aryl, -substituted aryl, —O-alkyl, -halo, -cyano, and -nitro; and
- wherein $R^7$ is selected from the group consisting of -hydrogen, -alkyl, -alkenyl, -fluoroalkyl, -fluoroalkenyl, -pyranyl, and -adamantyl,
- $L^-$ is selected from the group consisting of a sulfonate compound, $BF_4^-$, $PF_6^-$, and $SbF_6^-$; and
- $X^+$ is selected from the group consisting of a sulfonium compound and an ionium compound.

2. The photoacid generator of claim 1 having the structure:

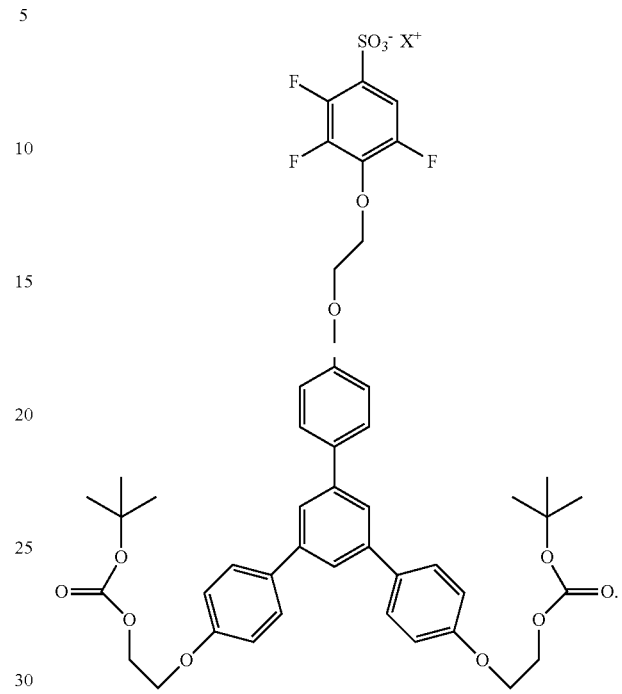

3. The photoacid generator of claim 1 having the structure:

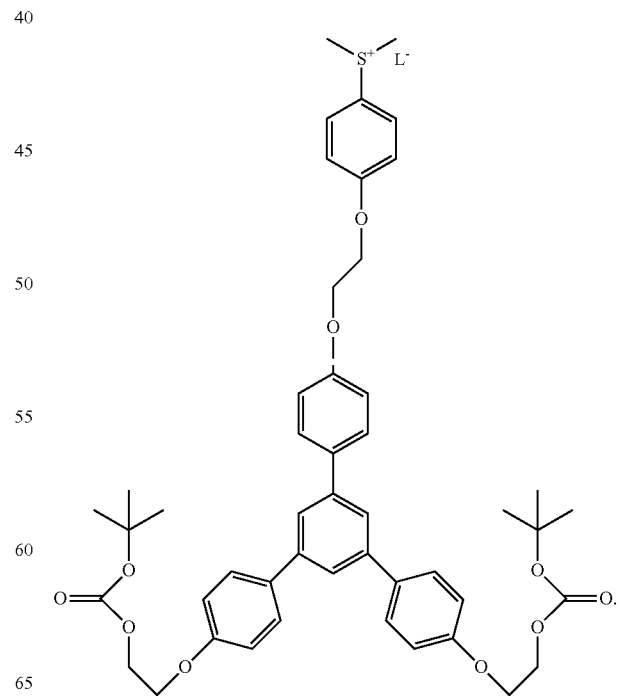

4. The photoacid generator of claim 1 having the structure:
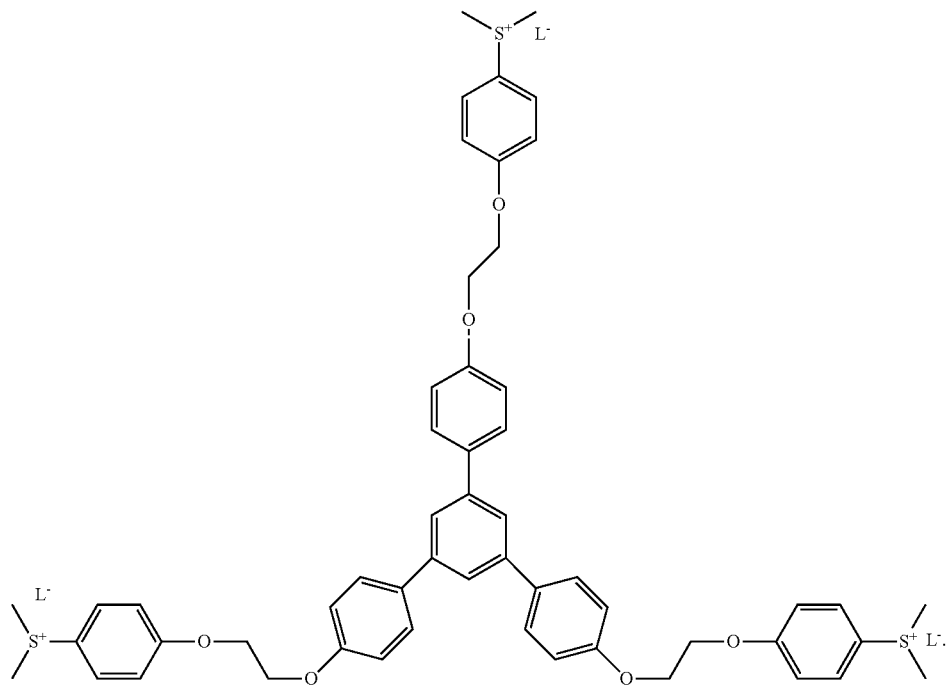
5. The photoacid generator of claim 1 having the structure:
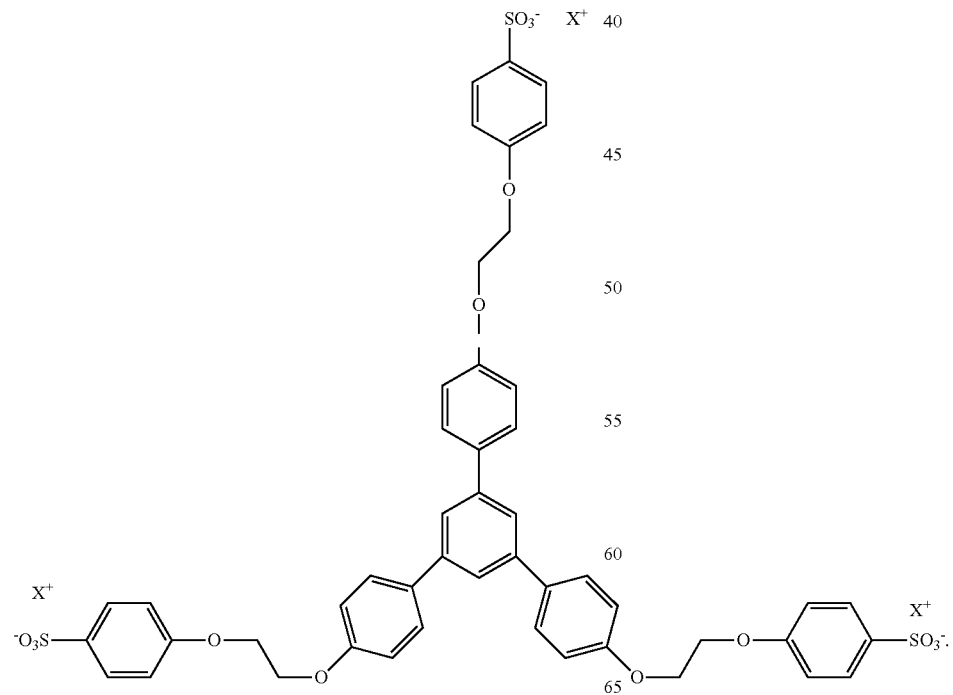

6. The photoacid generator of claim 1 having the structure:

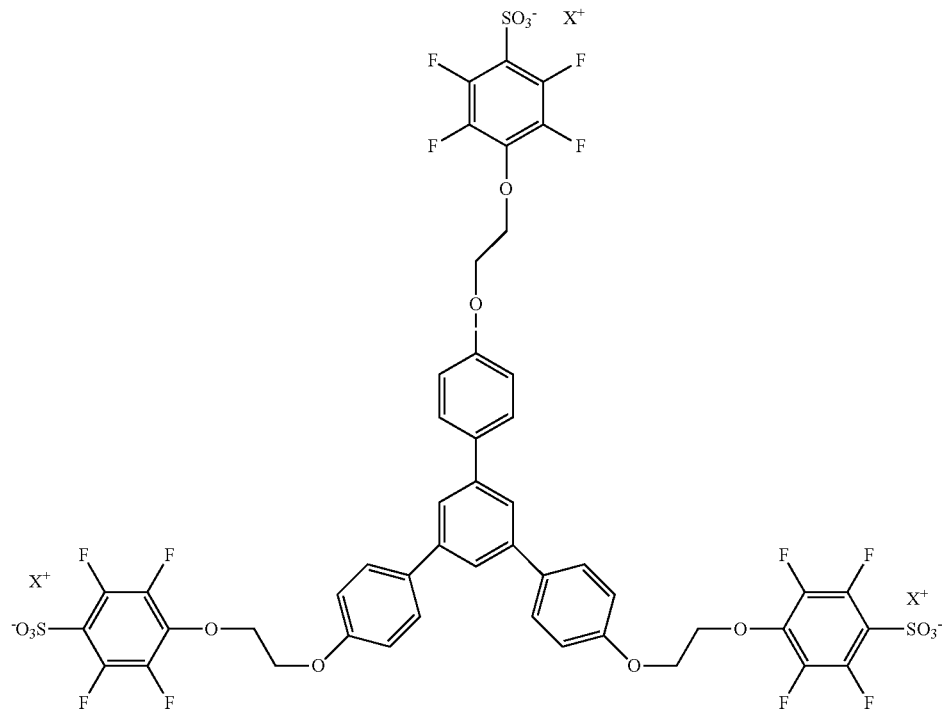

7. A dendrimer of Formula (IV):

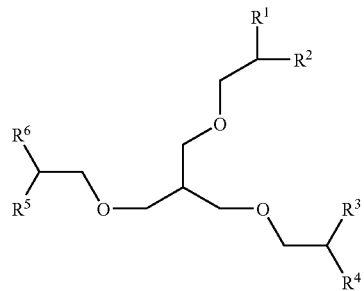

wherein $R^1$, $R^2$, $R^3$, $R^4$, $R^5$, and $R^6$ are independently selected from the group consisting of:

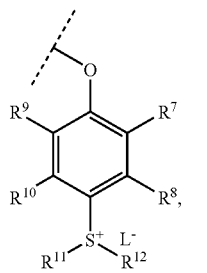

and —O—C(O)—O—$R^{13}$ wherein $R^7$, $R^8$, $R^9$, $R^{10}$, $R^{11}$, and $R^{12}$ are independently selected from the group consisting of -hydrogen, -alkyl, -alkylene, -fluoroalkyl, -fluoroalkenyl, -aryl, -substituted aryl, —O-alkyl, -halo, -cyano, and -nitro; and wherein $R^{13}$ is selected from the group consisting of -hydrogen, -alkyl, -alkenyl, -fluoroalkyl, -fluoroalkenyl, -pyranyl, and -adamantyl, $L^-$ is selected from the group consisting of a sulfonate compound, $BF_4^-$, $PF_6^-$, and $SbF_6^-$; and $X^+$ is selected form the group consisting of a sulfonium compound and an ionium compound.

8. The dendrimer of claim 7, wherein $R^1$ through $R^6$ are independently selected from the group consisting of:

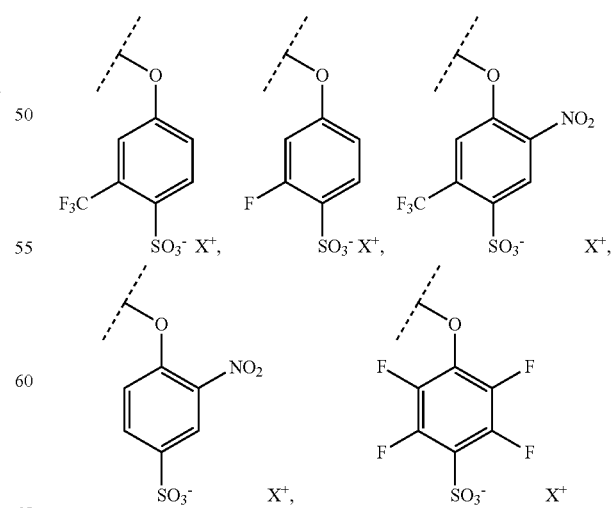

and —O—C(O)—O—$R^{13}$.

9. A lithographic resist comprising a photoacid generator selected from the group consisting of:

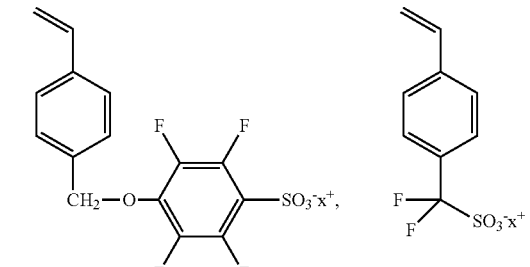

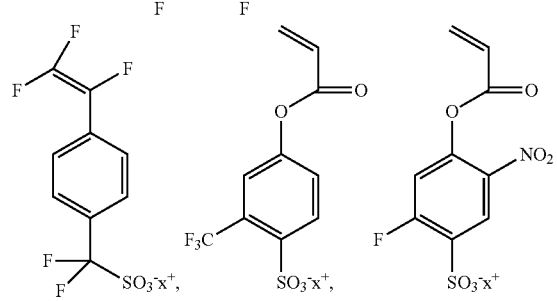

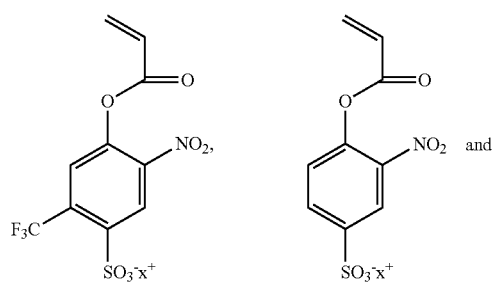

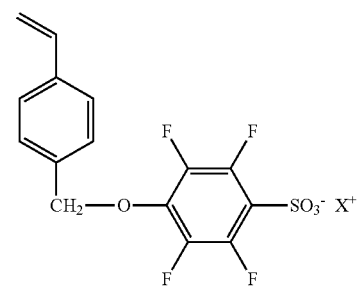

wherein X⁺ is selected from the group consisting of a sulfonium compound and an ionium compound.

10. The lithographic resist of claim 9, wherein the photoacid generator is

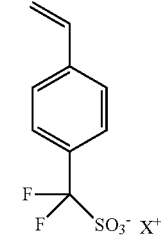

wherein X⁺ is selected from the group consisting of a sulfonium compound and an ionium compound.

11. The lithographic resist of claim 9, wherein the photoacid generator is

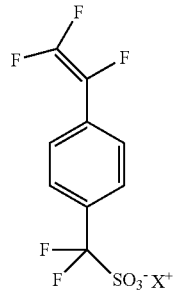

wherein X⁺ is selected from the group consisting of a sulfonium compound and an ionium compound.

12. The lithographic resist of claim 9, wherein the photoacid generator is

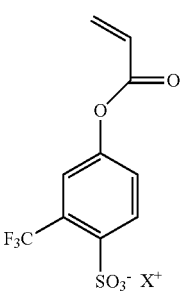

wherein X⁺ is selected from the group consisting of a sulfonium compound and an ionium compound.

13. The lithographic resist of claim 9, wherein the photoacid generator is

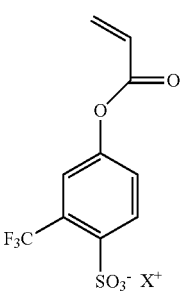

wherein X⁺ is selected from the group consisting of a sulfonium compound and an ionium compound.

14. The lithographic resist of claim 9, wherein the photoacid generator is

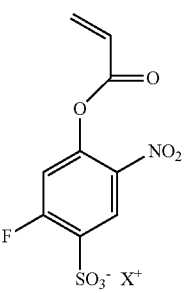

wherein X⁺ is selected from the group consisting of a sulfonium compound and an ionium compound.

15. The lithographic resist of claim 9, wherein the photoacid generator is

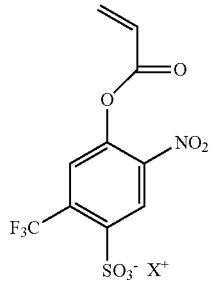

wherein X⁺ is selected from the group consisting of a sulfonium compound and an ionium compound.

16. The lithographic resist of claim 9, wherein the photoacid generator is

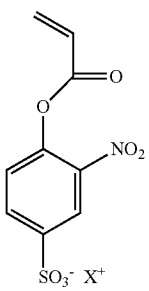

wherein X⁺ is selected from the group consisting of a sulfonium compound and an ionium compound.

17. A lithographic resist comprising an adamantyl component and a photoacid generating component, wherein the photoacid generating component is selected from the group consisting of:

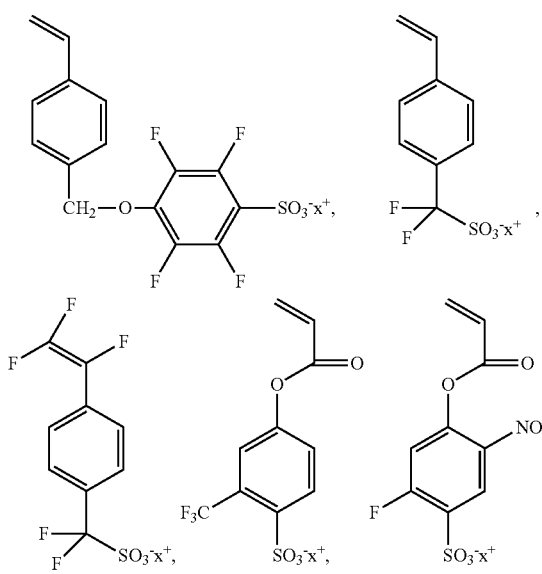

-continued

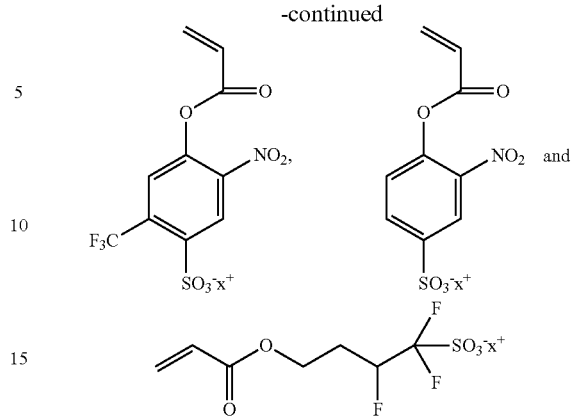

wherein X⁺ is selected from the group consisting of a sulfonium compound and an ionium compound.

18. The lithographic resist of claim 17 further comprising a hydroxystyrene component.

19. The lithographic resist of claim 17 further comprising a γ-butyrolactone component.

20. A lithographic resist comprising a photoacid generator of Formula (III):

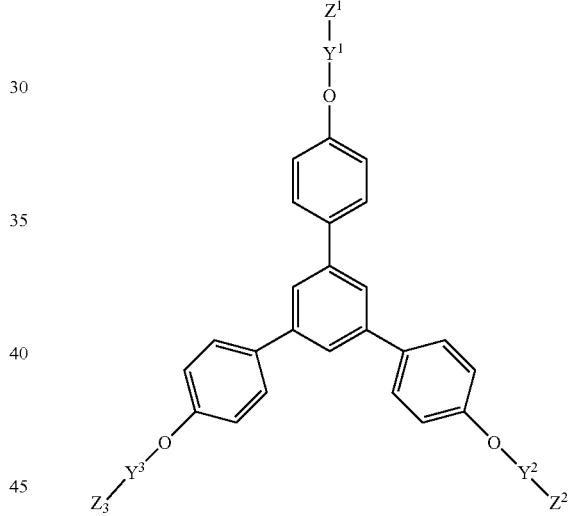

wherein
$Y^1$, $Y^2$, and $Y^3$ are independently selected from the group consisting of alkylene, alkenylene, fluoroalkylene, and fluoroalkenylene;
$Z^1$, $Z^2$, and $Z^3$ are independently selected from the group consisting of:

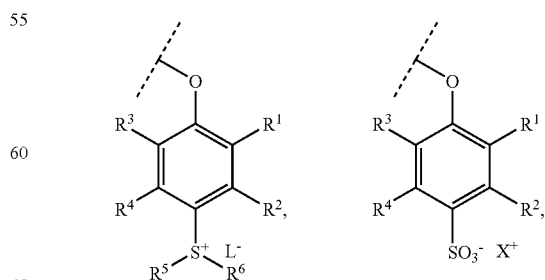

and —O—C(O)—O—$R^7$ wherein $R^1$, $R^2$, $R^3$, $R^4$, $R^5$, and $R^6$ are independently selected from the group consisting of -hydrogen, -alkyl, -alkylene, -fluoroalkyl, -fluoroalkenyl, -aryl, -substituted aryl, —O-alkyl, -halo, -cyano, and -nitro; and wherein $R^7$ is selected from the group consisting of -hydrogen, -alkyl, -alkenyl, -fluoroalkyl, -fluoroalkenyl, -pyranyl, and -adamantyl;

$L^-$ is selected from the group consisting of a sulfonate compound, $BF_4^-$, $PF_6^-$, and $SbF_6^-$; and $X^+$ is selected from the group consisting of a sulfonium compound and an ionium compound, wherein the lithographic resist does not comprise a polymeric component.

21. The lithographic resist of claim 20, wherein the photoacid generator is selected from the group consisting of:

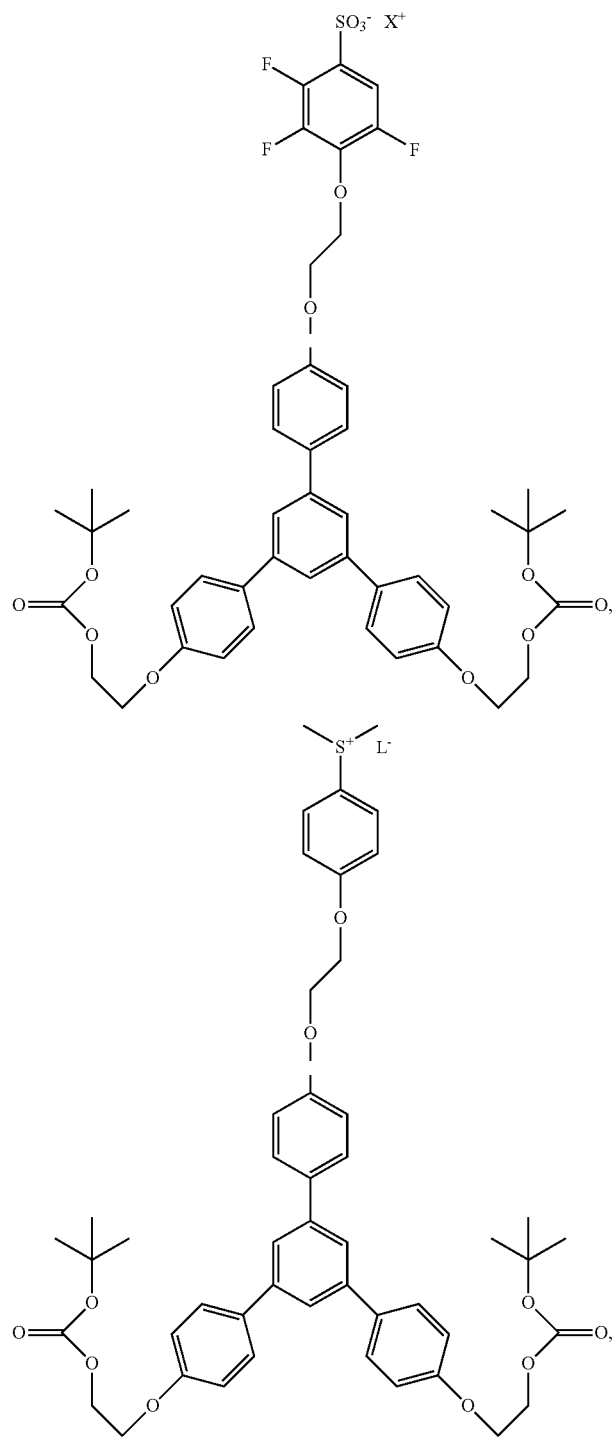

-continued
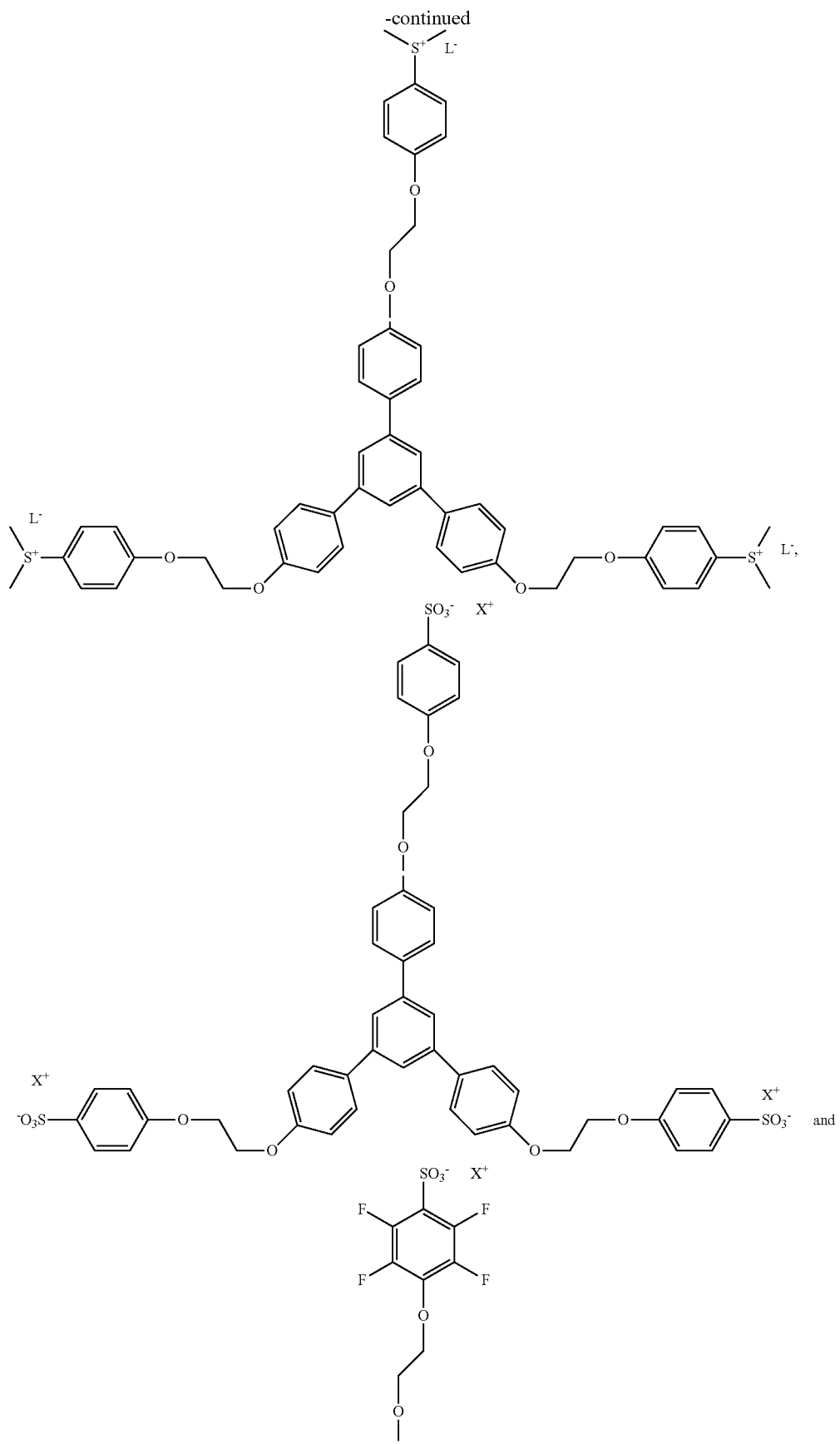

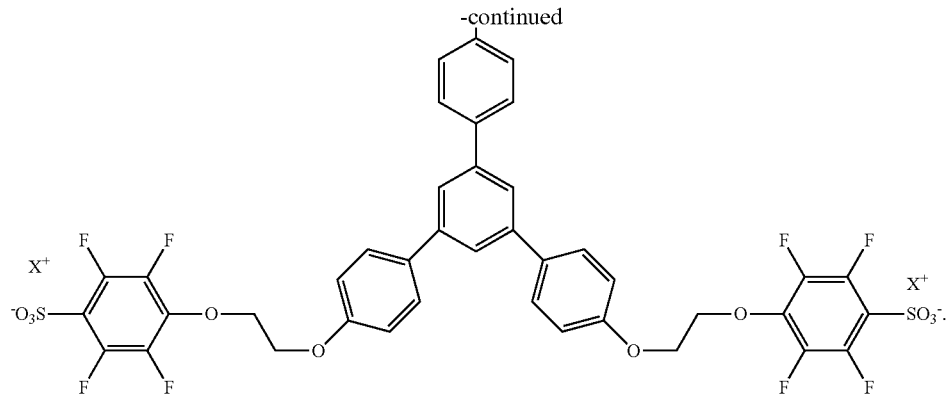

22. The lithographic resist of claim 20 further comprising an adamantyl component.

23. The lithographic resist of claim 22 further comprising a hydroxystyrene component.

24. The lithographic resist of claim 22 further comprising a γ-butyrolactone component.

25. A lithographic resist comprising a dendrimer of Formula (IV):

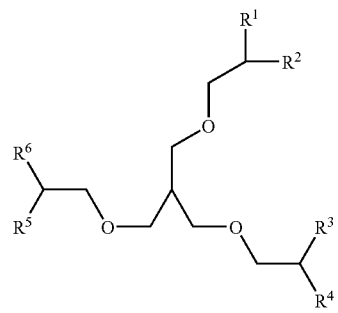

wherein $R^1$, $R^2$, $R^3$, $R^4$, $R^5$, and $R^6$ are independently selected from the group consisting of:

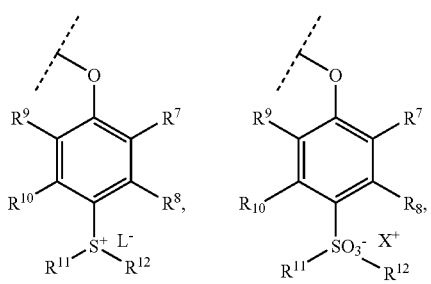

and —O—C(O)—O—$R^{13}$ wherein $R^7$, $R^8$, $R^9$, $R^{10}$, $R^{11}$, and $R^{12}$ are independently selected from the group consisting of -hydrogen, -alkyl, -alkylene, -fluoroalkyl, -fluoroalkenyl, -aryl, -substituted aryl, —O-alkyl, -halo, -cyano, and -nitro; and wherein $R^{13}$ is selected from the group consisting of -hydrogen, -alkyl, -alkenyl, -fluoroalkyl, -fluoroalkenyl, -pyranyl, and -adamantyl, $L^-$ is selected from the group consisting of a sulfonate compound, $BF_4^-$, $PF_6^-$, and $SbF_6^-$; and $X^+$ is selected form the group consisting of a sulfonium compound and an ionium compound.

26. The lithographic resist of claim 25, wherein $R^1$ through $R^6$ are independently selected from the group consisting of:

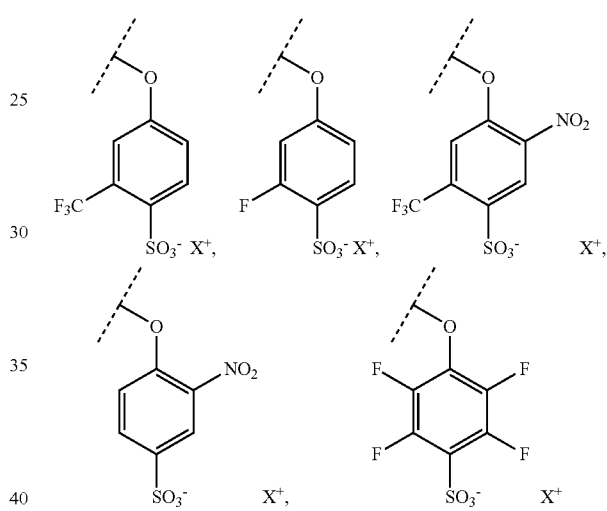

and —O—C(O)—O—$R^{13}$.

27. The lithographic resist of claim 25 further comprising an adamantyl component.

28. The lithographic resist of claim 27 further comprising a hydroxystyrene component.

29. The lithographic resist of claim 27 further comprising a y-butyrolactone component.

30. A method for producing a lithographic resist comprising:

blending a photoacid generating component with a first component, wherein the photoacid generating component is selected from the group consisting of:

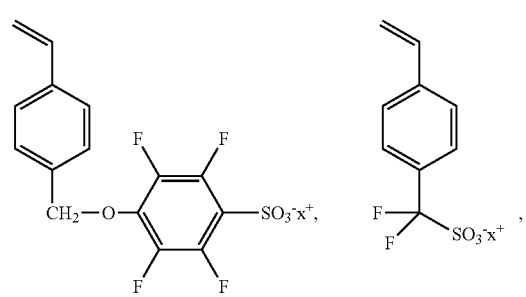

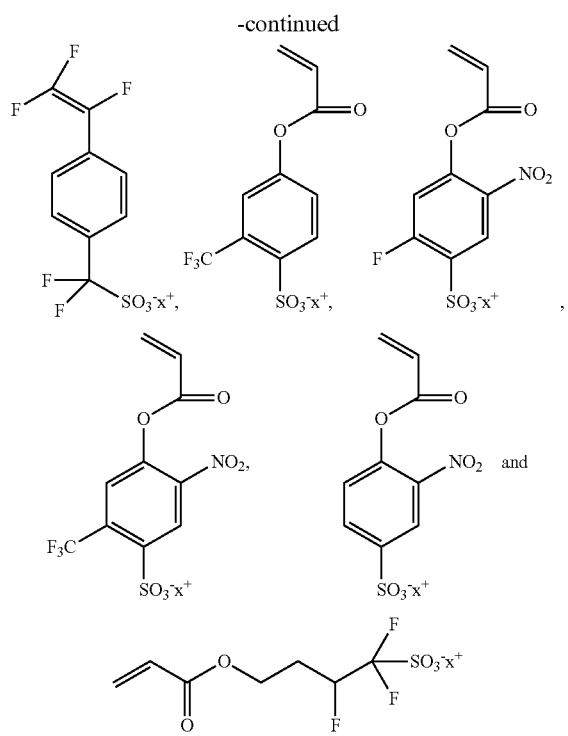

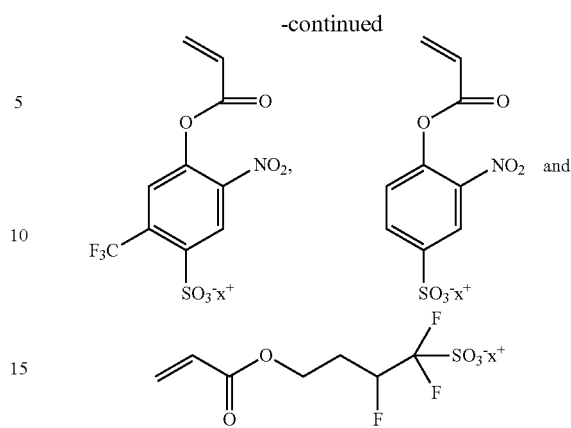

wherein X⁺ is selected from the group consisting of a sulfonium compound and an ionium compound.

31. The method of claim 30, wherein the first component comprises an adamantyl component.

32. A method for producing a lithographic resist comprising:

copolymerizing a first component and a photoacid generating component, wherein the photoacid generating component is selected from the group consisting of:

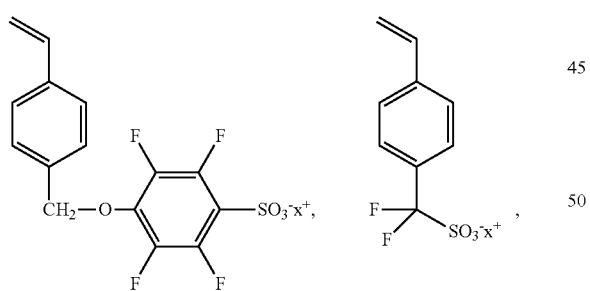

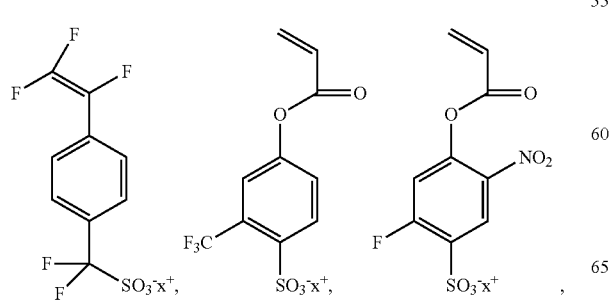

wherein X⁺ is selected from the group consisting of a sulfonium compound and an ionium compound.

33. The method of claim 32, wherein the first component comprises a first monomer, first oligomer, or a first polymer.

34. A photoacid generator having the structure:

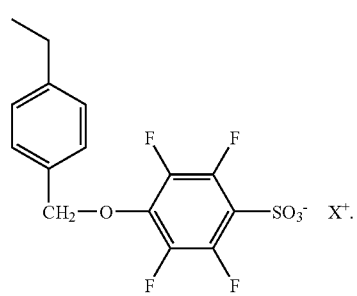

35. A photoacid generator having the structure:

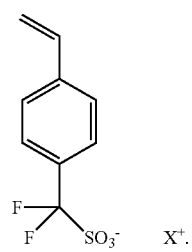

36. A photoacid generator having the structure:

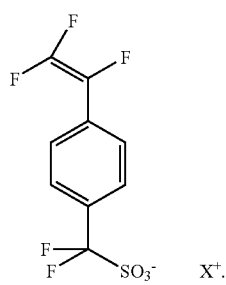

37. A photoacid generator having the structure:

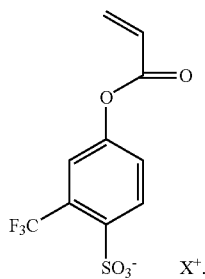

38. A photoacid generator having the structure:

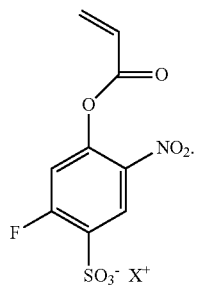

39. A photoacid generator having the structure:

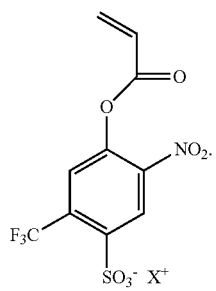

40. A photoacid generator having the structure:

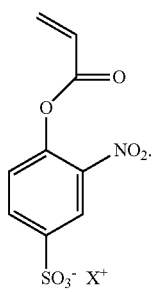

41. A photoacid generator having the structure:

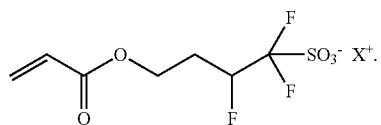

42. A lithographic resist comprising a photoacid generator having the structure:

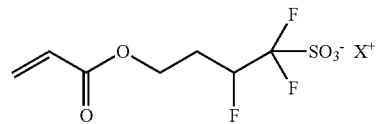

wherein
  $X^+$ is selected from the group consisting of a sulfonium compound and an ionium compound.

43. A method of producing a lithographic resist comprising:
  blending a photoacid generating component with a first component, wherein the photoacid generating component comprises a photoacid generator having the structure:

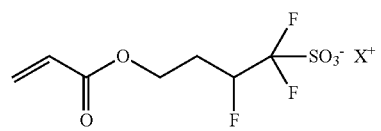

wherein
  $X^+$ is selected from the group consisting of a sulfonium compound and an ionium compound.

44. A method of producing a lithographic resist comprising:
  copolymerizing a first component and a photoacid generating component, wherein the photoacid generating component comprises a photoacid generator having the structure:

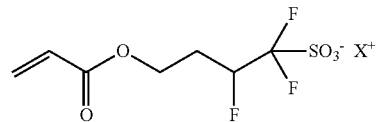

wherein
  $X^+$ is selected from the group consisting of a sulfonium compound and an ionium compound.

* * * * *